United States Patent
Gao et al.

(10) Patent No.: US 7,052,591 B2
(45) Date of Patent: May 30, 2006

(54) ELECTRODEPOSITION OF REDOX POLYMERS AND CO-ELECTRODEPOSITION OF ENZYMES BY COORDINATIVE CROSSLINKING

(75) Inventors: Zhiqiang Gao, Austin, TX (US); Adam Heller, Austin, TX (US); Murielle Dequaire, Dijon (FR)

(73) Assignee: TheraSense, Inc., Alameda, CA (US)

( * ) Notice: Subject to any disclaimer, the term of this patent is extended or adjusted under 35 U.S.C. 154(b) by 413 days.

(21) Appl. No.: 10/251,513

(22) Filed: Sep. 19, 2002

(65) Prior Publication Data

US 2003/0168338 A1   Sep. 11, 2003

Related U.S. Application Data

(60) Provisional application No. 60/324,078, filed on Sep. 21, 2001.

(51) Int. Cl.
    *C25D 13/04*   (2006.01)
(52) U.S. Cl. .................. 204/490; 205/316; 205/317
(58) Field of Classification Search ............... 204/490; 205/316, 317
    See application file for complete search history.

(56) References Cited

U.S. PATENT DOCUMENTS

| | | | |
|---|---|---|---|
| 4,820,399 A | 4/1989 | Senda et al. | |
| 5,262,035 A | 11/1993 | Gregg et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,651,869 A | 7/1997 | Yoshioka et al. | |
| 5,665,222 A | 9/1997 | Heller et al. | |
| 5,906,921 A | 5/1999 | Ikeda et al. | |
| 6,251,260 B1 | 6/2001 | Heller et al. | |
| 6,281,006 B1 | 8/2001 | Heller et al. | |
| 6,340,421 B1 | 1/2002 | Vachon et al. | |
| 6,436,255 B1 | 8/2002 | Yamamoto et al. | |
| 6,599,407 B1 | 7/2003 | Taniike et al. | |

(Continued)

FOREIGN PATENT DOCUMENTS

WO    WO 99/67019    12/1999

(Continued)

OTHER PUBLICATIONS

A. Heller, "Electrical Connection of Enzyme Redox Centers to Electrodes", J. Phys. Chem., 1992, 96, pp. 3579-3587.*

(Continued)

*Primary Examiner*—Kishor Mayekar
(74) *Attorney, Agent, or Firm*—Parsons Hsue & de Runtz LLP

(57) ABSTRACT

Thin films of transition metal complex-based redox polymers are electrodeposited on electrodes. When hydrated, an electrodeposited film conducts electrons by electron exchange between backbone-bound, but mobile, functional segments of its redox polymer constituents. These functional segments, or redox complexes, have labile ligands in their inner coordination spheres. The backbones of the redox polymers have strongly coordinating ligands. Electrodeposition results from coordinative crosslinking by exchange of labile ligands and strongly coordinating ligands between polymer chains. When a biological macromolecule or protein, such as a redox enzyme, is added to the solution from which the redox polymer is electrodeposited, it is co-electrodeposited on the electrode surface. When the co-deposited film contains redox enzymes, for example, the modified electrode may be used to catalyze the electrooxidation or electroreduction of substrates of the enzymes. Electrodes modified according to the invention also have application in chemical or biological assays.

66 Claims, 10 Drawing Sheets

U.S. PATENT DOCUMENTS

| | | |
|---|---|---|
| 6,740,215 B1 | 5/2004 | Nakaminami et al. |
| 6,885,196 B1 | 4/2005 | Taniike et al. |
| 2002/0001799 A1 | 1/2002 | Heller et al. |
| 2002/0008038 A1 | 1/2002 | Heller et al. |
| 2002/0081588 A1 | 6/2002 | De Lumley-woodyear et al. |
| 2003/0077772 A1 | 4/2003 | Shah et al. |
| 2004/0074785 A1 | 4/2004 | Holker et al. |

FOREIGN PATENT DOCUMENTS

| | | | |
|---|---|---|---|
| WO | WO 99/67628 | * | 12/1999 |

OTHER PUBLICATIONS

Saveant, "Electron Hopping Between Localized Sites. Effect of Ion Pairing on Diffusion and Migration. General Rate Laws and Steady-State Responses." *J. Phys. Chem.* 1988, 92, pp. 4526-4532.

Andrieux et al., "Electroneutrality Coupling of Electron Hopping between Localized Sites with Electroinactive Counterion Displacement," *J. Phys. Chem.* 1988, 92, pp. 6761-6767.

Lyons et al., "Charge Percolation in Electroactive Polymer Films," *J. Chem. Soc, Faraday Trans.* 1990, 86, pp. 2905-2910.

Anson et al., "Ion Association and Electric Field Effects on Electron Hopping in Redox Polymers. Application to the $Os(bpy)_3^{3+/2+}$ Couple in Nafion," *J. Am. Chem. Soc.* 1991,113, pp. 1922-1932.

Haas et al., "Mechanistic Investigations of Redox Polymer-Coated Electrodes Using Probe-Beam Deflection and Cyclic Voltammerty," *J. Chem. Soc, Faraday Trans.* 1991, 87, pp. 939-945.

Mathias et al., "An Alternating Current Impedance Model Including Migration and Redox-Site Interactions at Polymer-Modified Electrodes," *J. Phys. Chem.* 1992, 96, pp. 3174-3182.

Aoki et al., "Electron Diffusion Coefficients in Hydrogels Formed of Cross-Linked Redox Polymers," *J. Phys. Chem.* 1993, 97, pp. 11014-11019.

Aoki et al., "Effect of Quaternization on Electron Diffusion Coefficients for Redox Hydrogels Based on Poly(4-vinylpyridine)," *J. Phys. Chem.* 1995, 99, pp. 5102-5110.

Yang et al., "*In situ* FTIR Characterization of the Electrooxidation of Glassy Carbon Electrodes," *J. Appl. Electrochem.* 1995, 25, pp. 259-266.

Gao et al., "Electrodeposition of Redox Polymers and Co-Electrodeposition of Enzymes by Coordinative Crosslinking," *Angew.Chem. Int. Ed.*, Mar. 1, 2002, 41, No. 5, pp. 810-813.

Heller, "Electrical Connection of Enzyme Redox Centers to Electrodes," *J. Phys. Chem.* 1992, 96, pp. 3579-3587.

Rajagopalan, et al., "Electrical 'Wiring' of Glucose Oxidase in Electron Conducting Hydrogels," *Molecular Electronics*, 1997, pp. 241-253.

de Lumley-Woodyear et al., "Polyacrylamide-Based Redox Polymer for Connecting Redox Centers of Enzymes to Electrodes," *Anal. Chem.* 1995, 67, pp. 1332-1338.

Lay, "cis-BIS(2,2'-Bipyridine-N,N') Complexes of Ruthenium (III)/(II) and Osmium (III)(II)," *Inorg. Chem.* 1986, 24, pp. 291-306.

Gregg et al., "Redox Polymer Films Containing Enzymes," *J. Phys. Chem.*, 1991, 95, pp. 5970-5975.

Maerker et al., "The Synthesis of Some 4,4'-Disubstituted 2,2'—Bipyridines," *J. Am. Chem. Soc*, 1958, 80, pp. 2475-2748.

Anderson et al., "Preparation and Characterization of 2,2'-Bipyridine-4,4'-disulphonic and 5-sulphonic Acids and their Ruthenium (II) Complexes. Excited-State Properties and Excited-State Electron-Transfer Reactions of Ruthenium (II) Complexes . . . " *Chem. Soc. Dalton Trans.*, 1985, pp. 2247-2261.

Kenausis et al., "'Wiring' Glucose Oxidase and Lactate Oxidase Within a Hydrogel Made with Poly(vinyl pyridine) Complexed with $[Os(4,4'\text{-dimethoxy-2,2'-bipyridine})_2 Cl]^{+/2+}$," *J. Chem. Soc., Faraday Trans.*, 1996, 92, pp. 4131-4136.

Forster et al., "Synthesis, Characterization, and Properties of a Series of Osmium- and Ruthenium-Containing Metallopolymers," *Macromolecules*, 1990, 23, pp. 4372-4377.

Barton et al., "the 'Wired' Laccase Cathode: High Current Density Electroreduction of $O_2$ to Water at + 0.7 V. (NHE) at pH 5," *J. Am. Chem. Soc.* 2001, 123, pp. 5802-5803.

Ohara et al., "Glucose Electrodes Based on Cross-Linked $[Os(bpy)^2Cl]^{+/2+}$ Complexed Poly(1-vinylimidazole) Films", *Anal. Chem.* 1993, 65, pp. 3512-3517.

Dequaire et al., "Screen Printing of Nucleic Acid Detecting Carbon Electrodes," *Anal. Chem.*, 2002, 74, pp. 4370-4377.

Bagel et al., "Subfemtomolar Determination of Alkaline Phosphatase at a Disposable Screen-Printed Electrode Modified with a Perfluorosulfonated Ionomer Film,", *Anal. Chem.* 1997, 69, pp. 4688-4694.

* cited by examiner

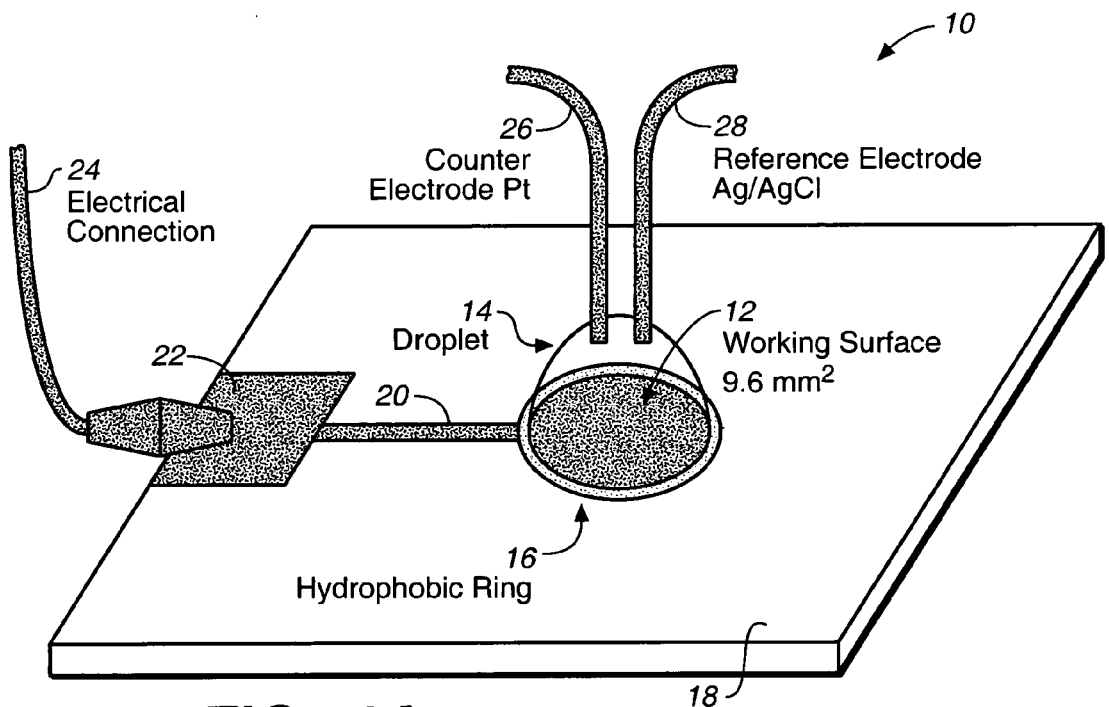
FIG._1A
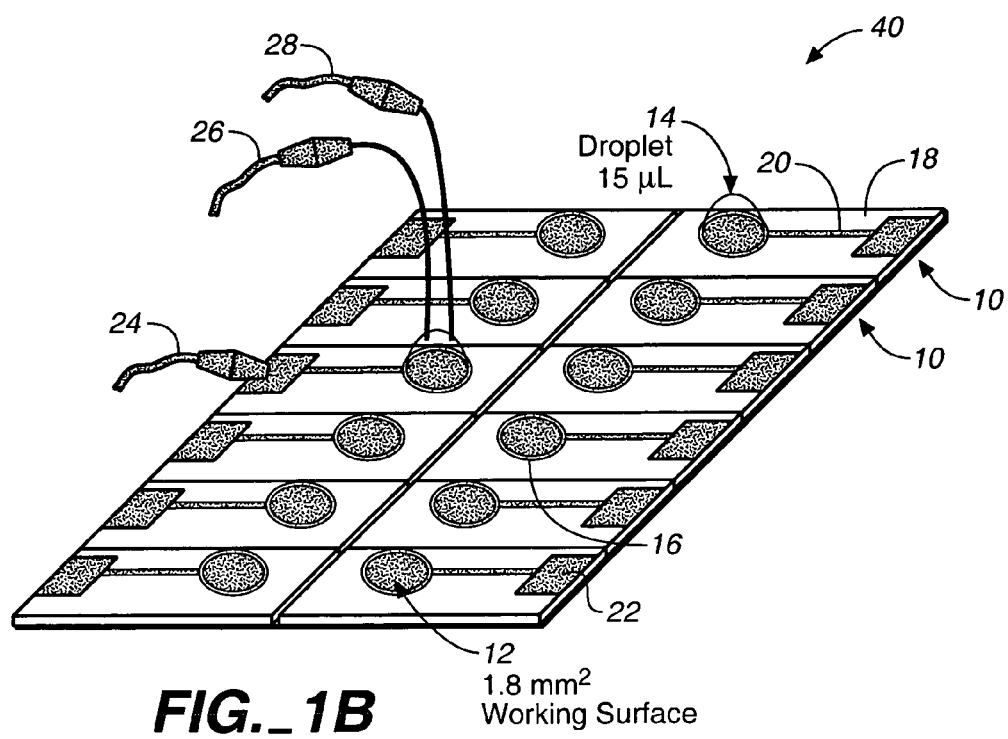
FIG._1B

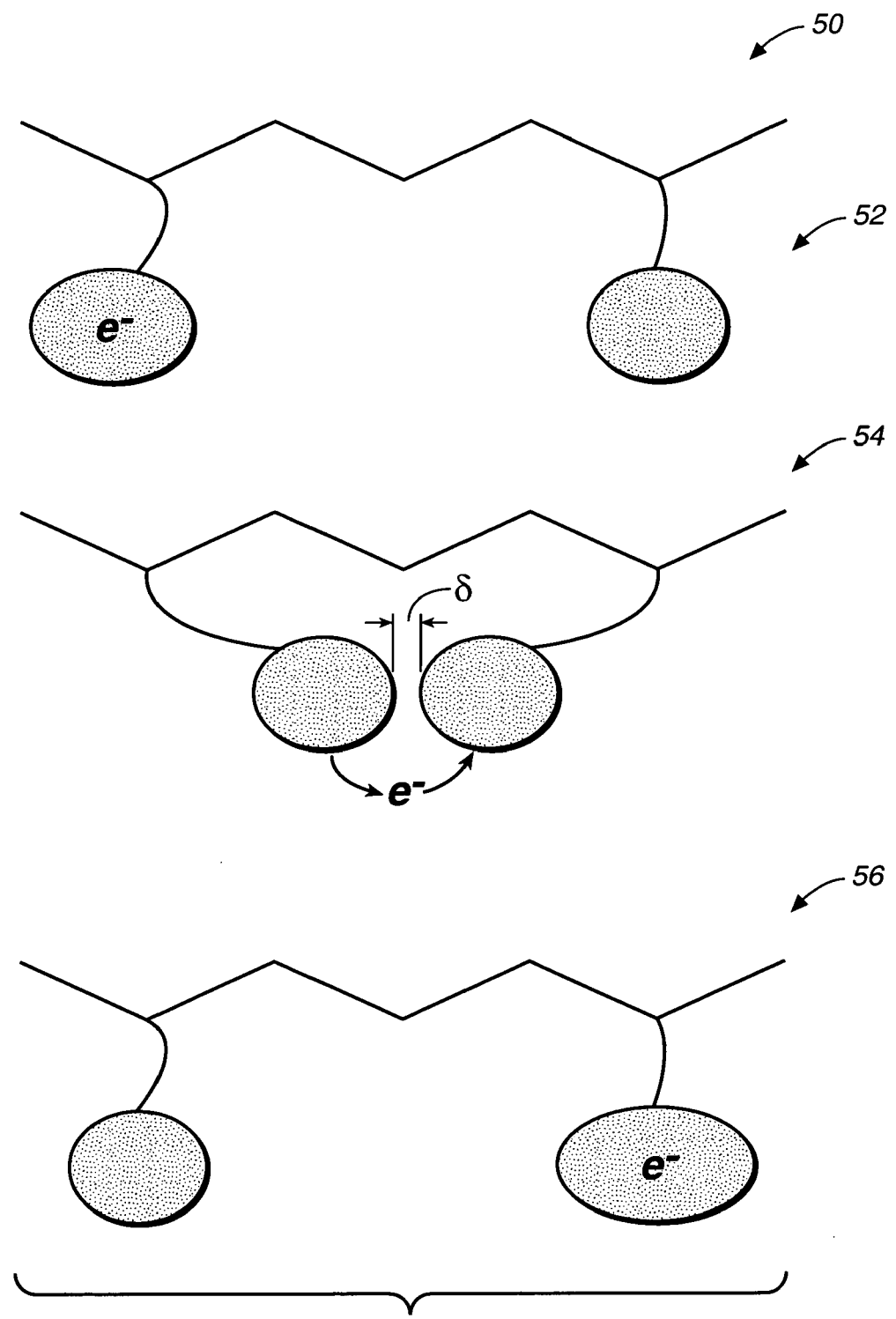
FIG._2

FIG._3
FIG._3A | FIG._3B | FIG._3C
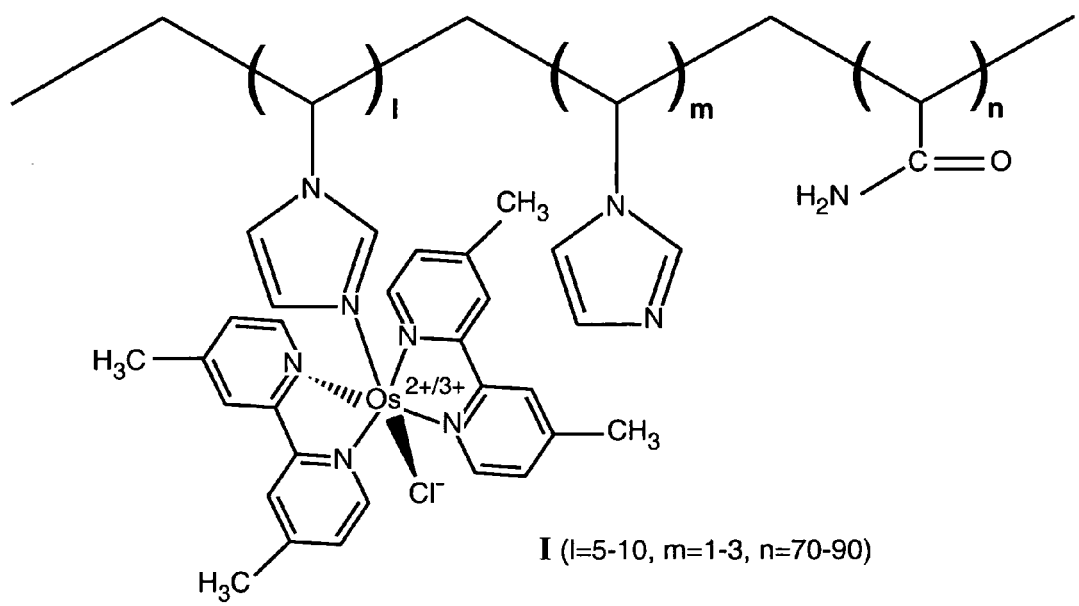
I (l=5-10, m=1-3, n=70-90)
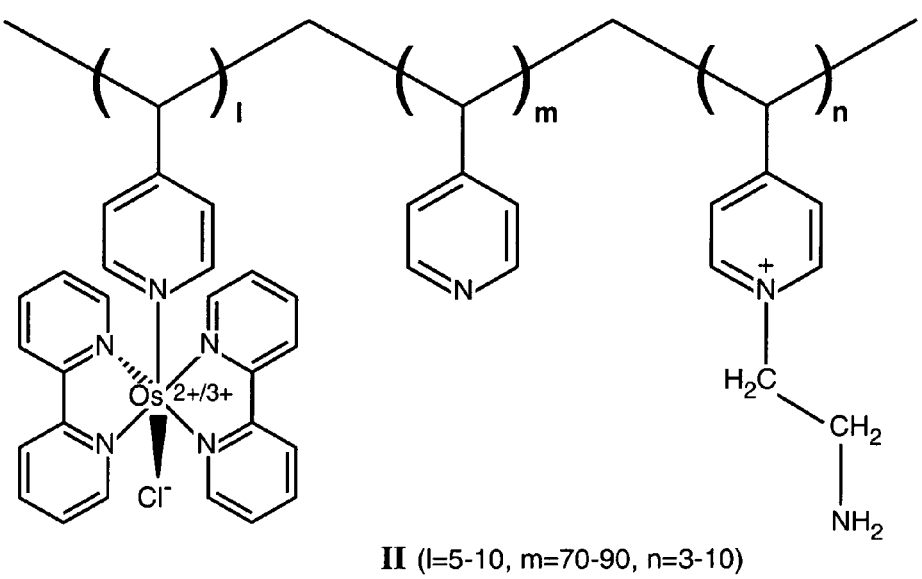
II (l=5-10, m=70-90, n=3-10)
FIG._3A

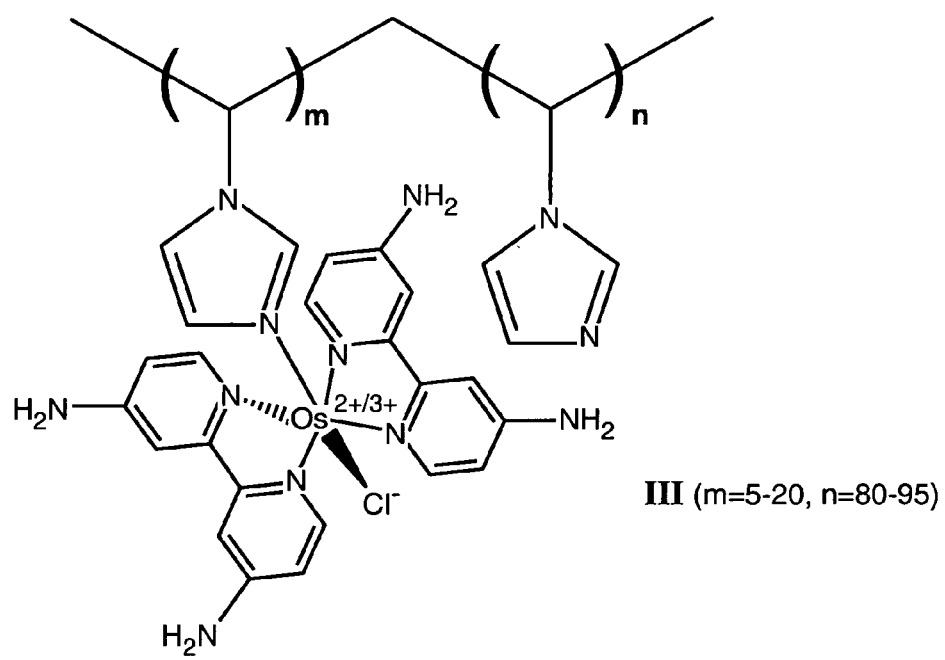
III (m=5-20, n=80-95)
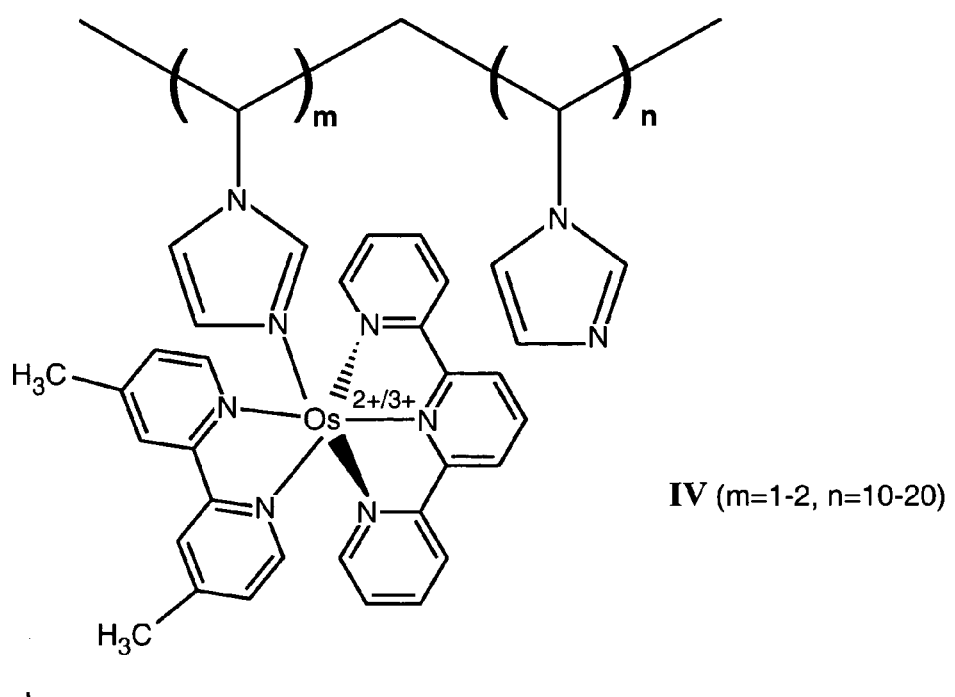
IV (m=1-2, n=10-20)
FIG._3B

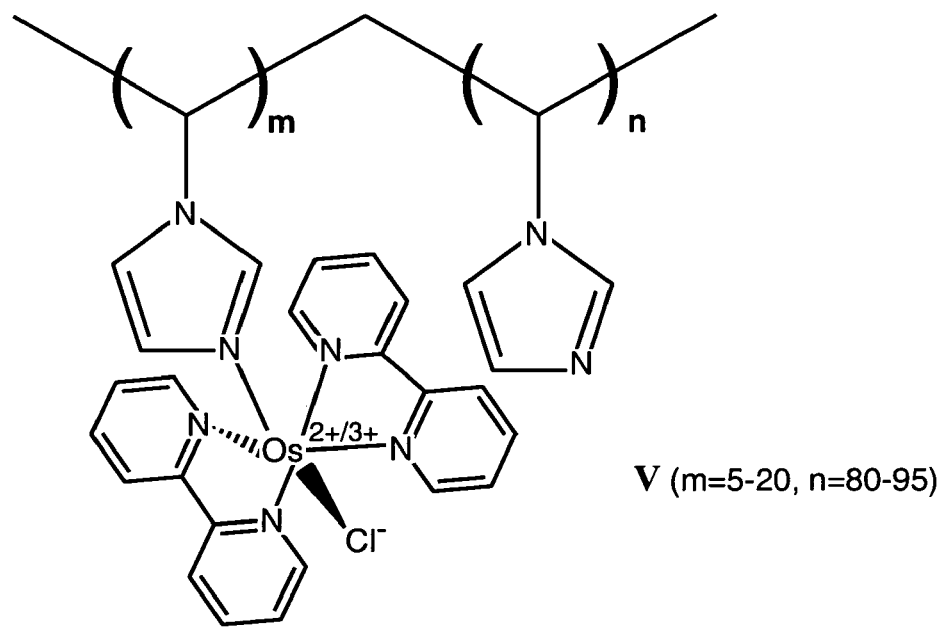
V (m=5-20, n=80-95)
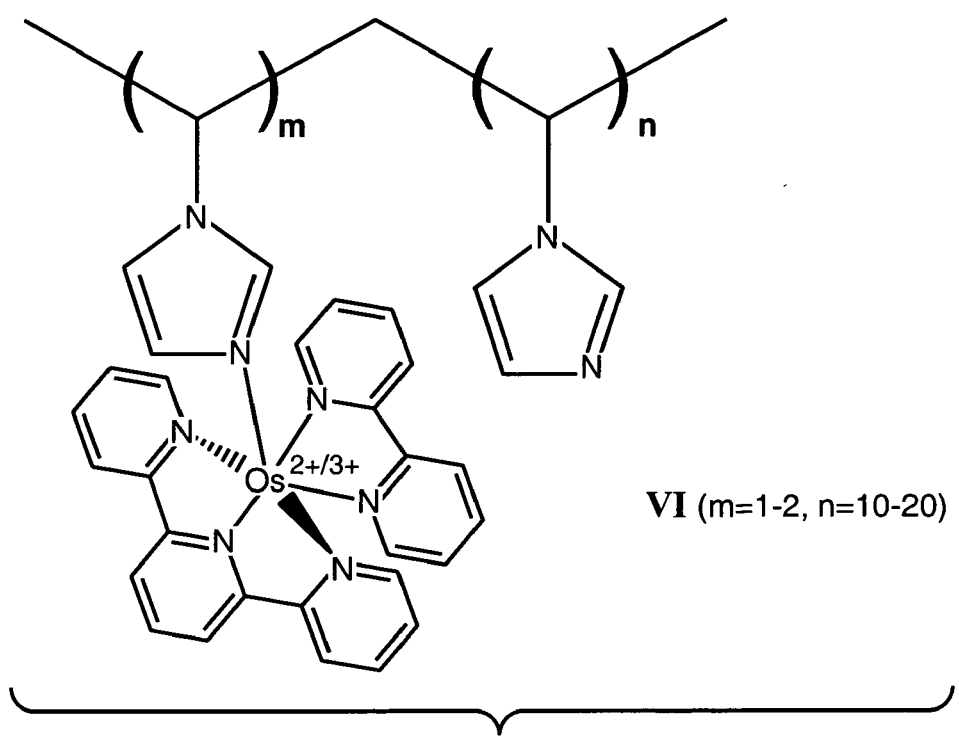
VI (m=1-2, n=10-20)
*FIG._3C*

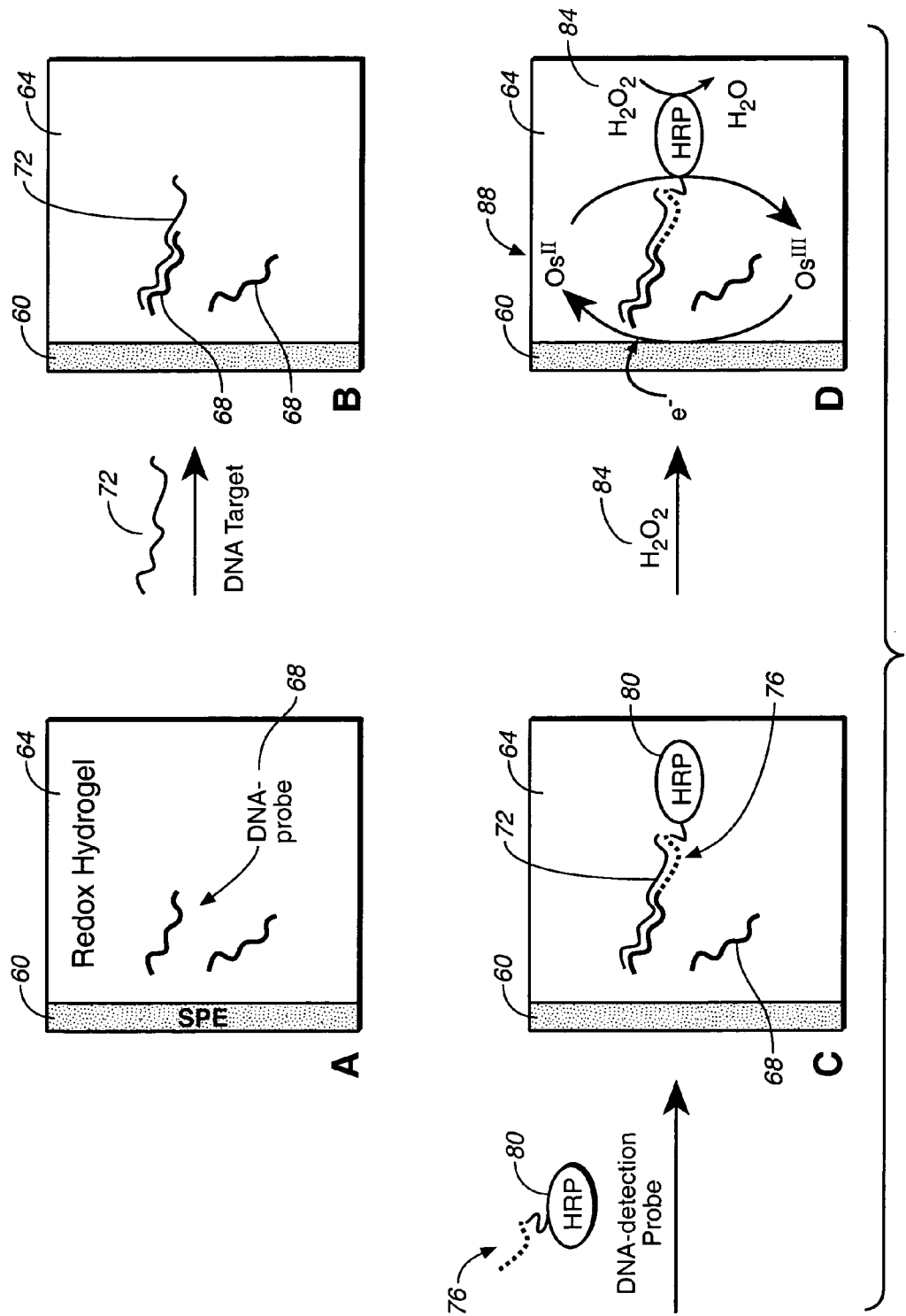
FIG._4

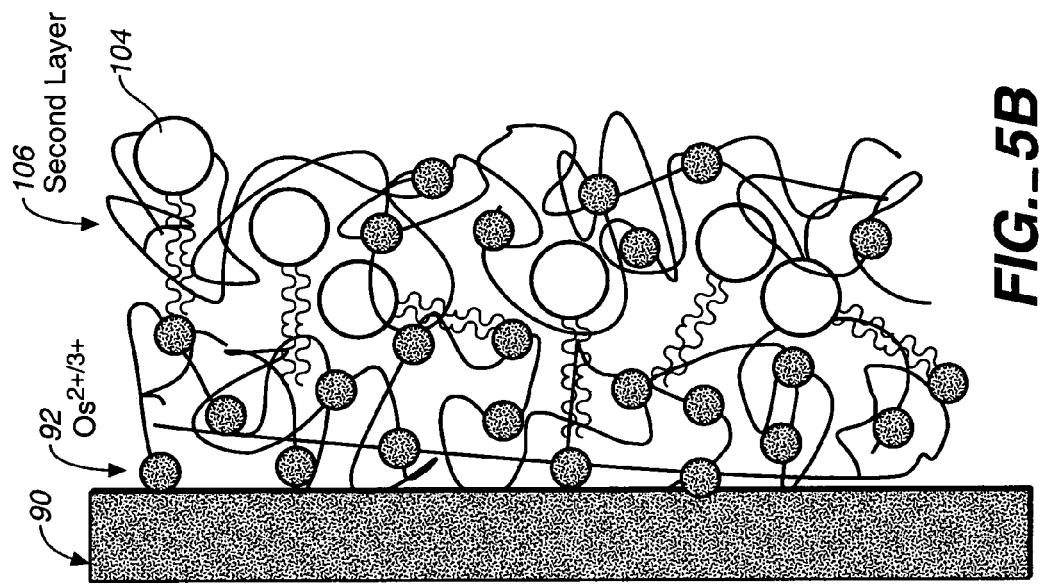
FIG._5B
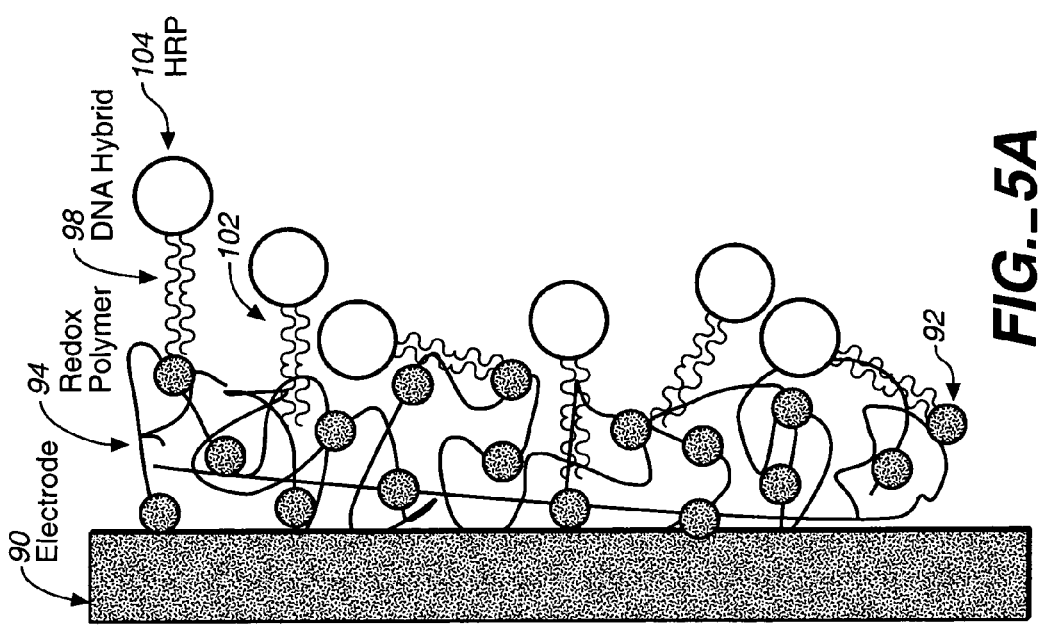
FIG._5A

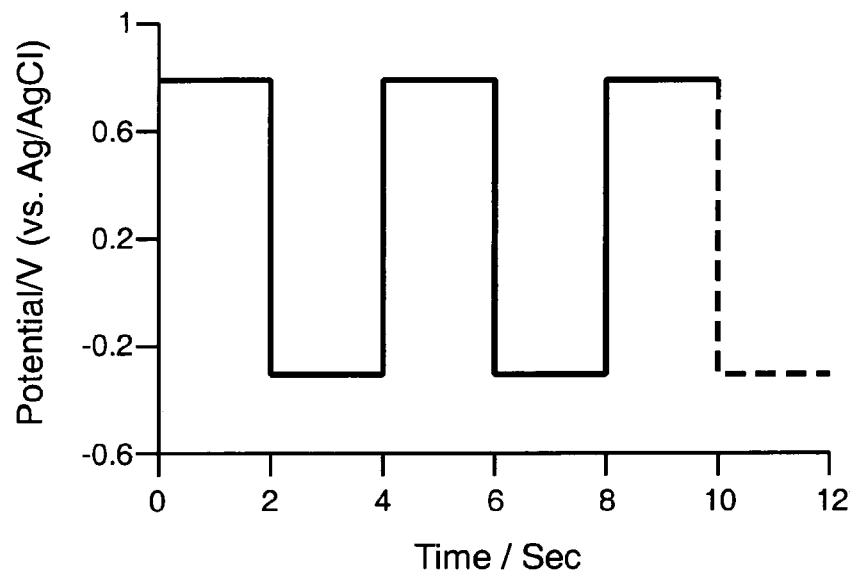
FIG._6
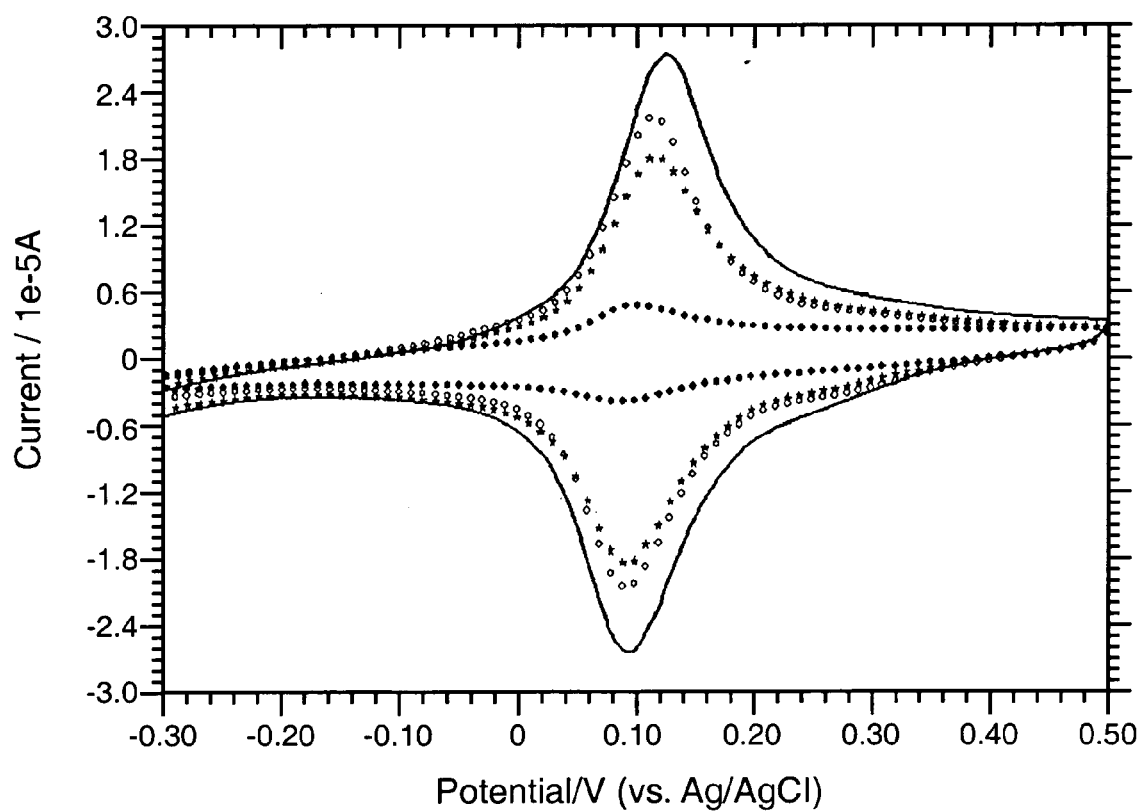
FIG._7

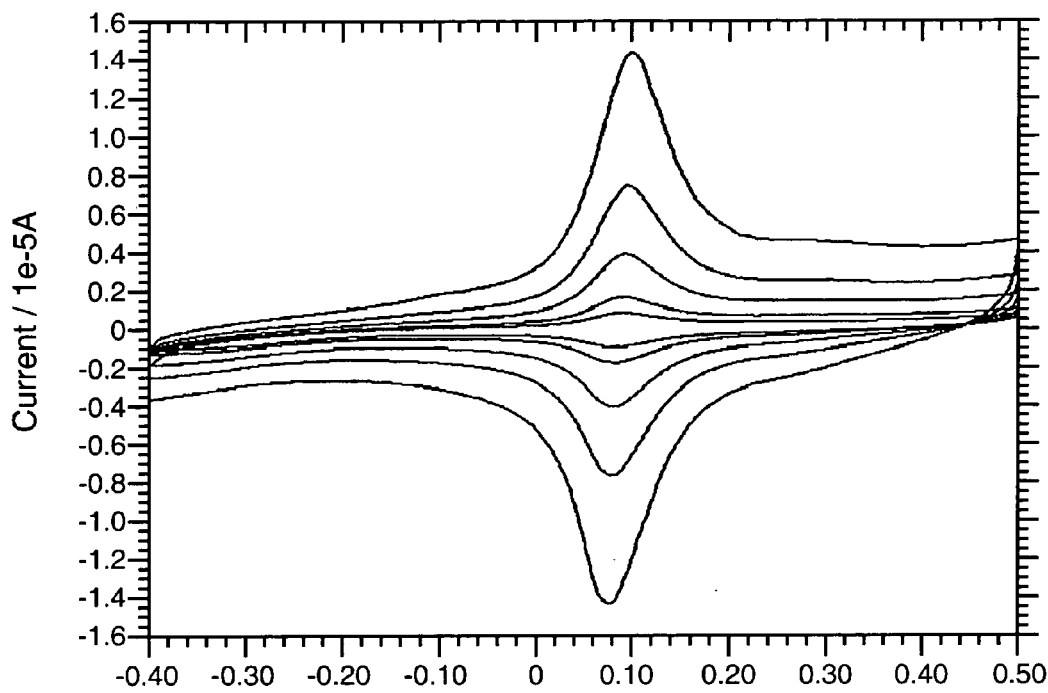
FIG._8
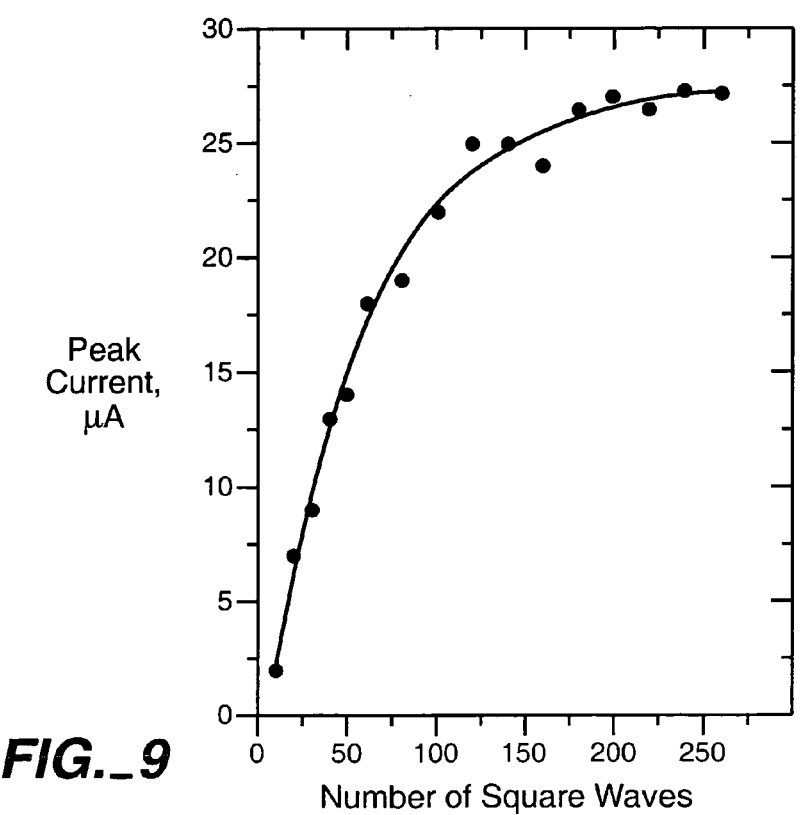
FIG._9

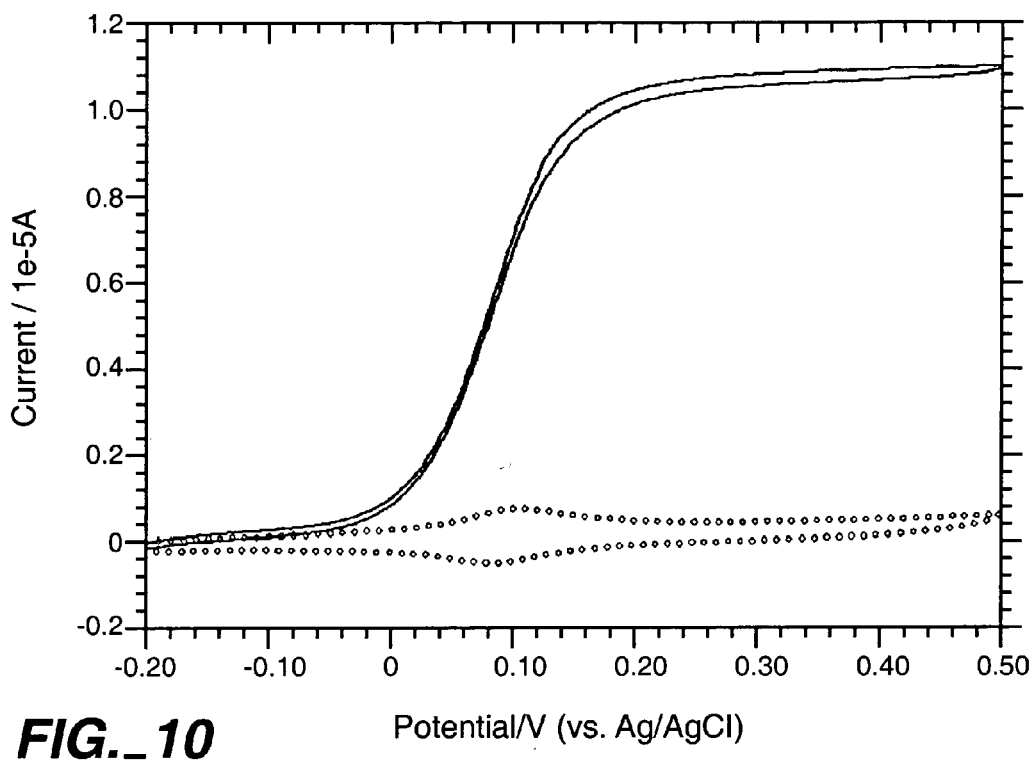
FIG._10
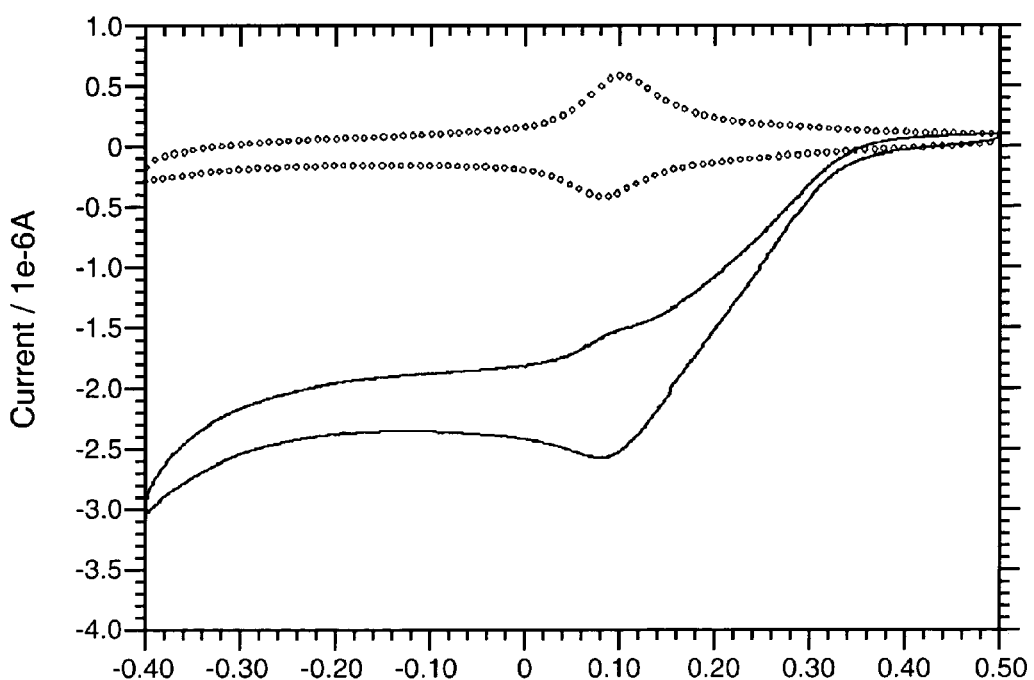
FIG._11

ELECTRODEPOSITION OF REDOX POLYMERS AND CO-ELECTRODEPOSITION OF ENZYMES BY COORDINATIVE CROSSLINKING

CROSS-REFERENCE TO RELATED APPLICATIONS

This application claims priority to U.S. Provisional Application Ser. No. 60/324,078 of Gary Binyamin, Adam Heller, Zhiqiang Gao, Hyug-Han Kim, Scott Calabrese Barton and Yongchao Zhang, entitled "Electrodeposition of Redox Polymers and Co-Electrodeposition of Enzymes by Coordinative Crosslinking", filed on Sep. 21, 2001, which application is incorporated herein in its entirety by this reference.

STATEMENT OF FEDERAL SPONSORSHIP

Some of the research described herein was performed in connection with a Contract/Cooperative Agreement Nos. DAAD17-01-D-0001 and DAAD17-01-D-0002 involving the United States Army Research Laboratory of the United States Government.

INCORPORATION BY REFERENCE OF MATERIAL SUBMITTED ON COMPACT DISC

An ASCII diskette and a duplicate copy thereof, containing the Sequence Listing for SEQ ID NO: 1 through SEQ ID NO: 7 disclosed herein, as well as a paper copy of the Sequence Listing, are submitted herewith and are incorporated herein in their entireties by this reference.

FIELD OF THE INVENTION

The present invention is generally related to the electrodeposition of redox polymers on electrodes, such as microelectrodes. The present invention is also generally related to the co-deposition of proteins, DNA and other biological macromolecules on such electrodes. The invention further relates to methods of preparing electrodes with electrodeposited films and methods of using such electrodes, such as using them in assays.

BACKGROUND OF THE INVENTION

Electrode surfaces have been coated with various polymeric materials for a variety of purposes. For example, in various applications, it has been desirable to coat electrode surfaces with polymeric materials that allow for the transmission of electric charges on the electrode surface. A process that is frequently used to coat an electrode surface with a conductive polymeric material involves the production, propagation, and combination of radical precursors to form the desired polymeric coating, such as a polyvinyl coating, on the electrode surface.

In certain applications, it is desirable to confine the transmission of electric charges to specific portions of the electrode surface. However, as electrodes have become smaller and smaller with advances in technology, it has become difficult to control the coating of the electrode surface to confine charge transmission on the electrode surface precisely enough for certain applications. For example, some electrodes of reduced size cannot be manufactured because it is not currently possible to coat the electrode surface precisely enough to prevent the entire electrode surface from becoming electroactive. Any improvement in the modification of electrode surfaces, and particularly, microelectrode surfaces, is therefore of considerable interest.

Polymer-coated electrodes may be used as electrochemical biosensors. For example, in a glucose biosensor, a working electrode coated with a redox polymer film that electrically connects or "wires" reaction centers of an enzyme, such as glucose oxidase, to the electrode, can be used to glucose that is electrocatalytically oxidized by the "wired" enzyme at the electrode surface. See, for example, A. Heller et al., U.S. Pat. No. 6,251,260. There is an increasing interest in miniaturizing biosensors, such as the glucose biosensor just described, particularly in the development of implantable biosensors.

Polymer-coated electrodes may also be used in the sensing of chemical and biological molecules, such as DNA-containing molecules. By way of example, an electrochemical system employing an electrode that is coated with a redox polymer film, in which sensor molecules and enzymes are immobilized, has been developed for use in affinity assays, such as sandwich-type immunoassays, for the detection of various biological ligands. See A. Heller et al., U.S. Pat. No. 6,281,006. Further by way of example, a multi-sensor array of electrodes, coated with a redox polymer film and nucleic acid sensor molecules, has been developed for the electrochemical recognition of nucleotide sequences. See De Lumley-Woodyear et al., U.S. patent application Publication No. 2002/0081588. The above-described redox polymer coatings may be electrodeposited on the electrodes. There is a keen interest in the refinement or further development of such sensors for chemical and biological assays, including the development of electrodeposition processes used to produce the sensors.

Many of the electrochemical biosensors marketed today, such as the glucose sensors used by diabetics to monitor blood glucose levels, are based on screen-printed carbon electrodes that are mass-produced at low cost. The development of electrodes with useful surface coatings, such as those suitable for glucose sensing, or for various chemical or biological assays, that can be mass-produced is of considerable interest. The development of means for electrodepositing useful coatings, such as thin, redox polymer films, on electrode surfaces, and particularly, on a mass-production basis, is similarly of interest.

BRIEF SUMMARY OF THE INVENTION

In the present invention, a redox polymer film, and preferably a thin film, is electrodeposited on an electrode surface. The redox polymer comprises a complex of a transition metal of Group VIII of the Periodic Table, such as a ruthenium or osmium complex, and preferably the latter. The redox polymer additionally comprises a labile ligand in an inner coordination sphere of the transition metal complex, as well as a strongly coordinating ligand. The labile ligand may be a halide, a pseudohalide, and a perchlorate, and is preferably a chloride ligand. The strongly coordinating ligand may be a nitrogen-containing ligand, such as an amine-containing, a pyridine-containing, or an imidazole-containing ligand, preferably, one of the latter two, that is linked to the redox polymer backbone. While strongly coordinating, this ligand is preferably not coordinated in the redox polymer prior to electrodeposition.

The redox polymers are provided at the electrode surface such that there are sufficient transition metal complex centers, such as $Os^{2+/3+}$ centers, at a desired portion of electrode surface for electrodeposition to occur. If the provision of redox polymers at the electrode surface is insufficient, electrodeposition of the redox polymer film will be insufficient or will not occur at all. According to some embodiments, the redox polymers may be electrodeposited from a small droplet, such as a 15–35 µL droplet, from an appropriately concentrated redox polymer solution. When the electrode surface is hydrophilic, a hydrophobic material may be used to confine the droplet to a desired portion of the electrode surface, such that the electrodeposition, and thus, surface electroactivity, will be appropriately confined.

Electrodeposition of the redox polymers involves the application of a potential or the application of one or more cycles of varying potential to the electrode surface. The electrodeposition is characterized by coordinative crosslinking by exchange of the labile ligand of one redox polymer with its own strongly coordinating ligand or with that of another redox polymer. When the concentration of transition metal complex centers at the electrode surface is high, as is preferred, the latter exchange will typically predominate. When an electrodeposited redox polymer film is hydrated, it conducts electrons by way of its backbone-bound, yet mobile, transition metal redox centers.

According to the present invention, a thin, redox polymer film may be electrodeposited on a surface any of a variety of electrodes, such as vitreous carbon electrodes or graphite electrodes. The electrode surface may be oxidized prior to the electrodeposition of the redox polymer film, although this is not necessary, particularly in the case of a graphite surface. The electrodeposited film may be confined to a very small area, such that it can be electrodeposited on a microelectrode, such as a screen-printed microelectrode that may be part of an electrode array.

In various embodiments of the present invention, redox polymers are electrodeposited from an aqueous solution, typically at around room temperature, at about neutral pH, and in about 200 seconds. A protein or other amine function-comprising biological macromolecule, such as a redox enzyme (an oxidase, a peroxidase, or a copper-containing enzyme), may be added to the solution from which the redox polymer is electrodeposited, such that the protein or macromolecule is co-electrodeposited, or may be otherwise incorporated into the redox polymer film. When the electrodes are electrochemically activated, the redox polymer film catalyzes the electrooxidation or electroreduction of a substrate of the protein or macromolecule, demonstrating that the redox centers of the film are effectively "wired" or electrically connected to the electrodes.

In various embodiments of the present invention, screen-printed carbon electrodes were successfully electrodeposited with redox polymer films and further modified to produce electrodes for biological assays. In an optimization of the electrodeposition and modification of such electrodes, electrochemical cells of 15–35 µL were able to detect 0.6 femtomoles of a DNA target. This result represents about a 25-fold reduction in detection limits as compared to earlier enzyme-amplified amperometric assays.

These and other aspects, features, and advantages of the present invention are described in the drawings and the description of the invention set forth below, or will be apparent or appreciated upon consideration thereof.

BRIEF DESCRIPTION OF THE DRAWINGS

FIG. 1A is a schematic illustration of an electrode that may be employed in embodiments of the present invention. FIG. 1B is a schematic illustration of an array of electrodes, wherein each electrode in the array is like that of FIG. 1B.

FIG. 2 is a schematic illustration of electron exchange of between segments of redox polymers that are electrodeposited on an electrode, such as that of FIG. 1A, according to embodiments of the present invention.

FIG. 3 illustrates molecular structures of redox polymers I, II, III and V that may be electrodeposited on an electrode, such as that of FIG. 1A, according to embodiments of the present invention, as well as molecular structures of two other redox polymers IV and VI that are used for comparison.

FIG. 4 is a schematic illustration of an assay, or sandwich-type assay, based on an electrode having a redox polymer electrodeposited thereon, according to an embodiment of the present invention.

FIGS. 5A and 5B are schematic illustrations an electrode having a single layer or a double layer, respectively, of a redox polymer film electrodeposited thereon, along with other components, for use in connection with an assay, such as a sandwich-type assay of FIG. 4, according to embodiments of the present invention.

FIG. 6 is a graphical representation of redox cycling in the form of square-wave potential cycling that may be used in the electrodeposition of redox polymers, such as redox polymers I, II, III and V of FIG. 3, on an electrode, such as that of FIG. 1A, according to embodiments of the present invention.

FIG. 7 is a graphical representation of cyclic voltammograms of a film of redox polymers I of FIG. 3, as electrodeposited on an electrode, at various oxidizing potentials.

FIG. 8 is a graphical representation of cyclic voltammograms of a fully annealed film of redox polymers I of FIG. 3, as electrodeposited on an electrode, at various scan rates.

FIG. 9 is a graphical representation of peak current versus the number of square waves in an electrodeposition of a film of redox polymers I of FIG. 3 on an electrode.

FIG. 10 is a graphical representation of cyclic voltammograms of a film of redox polymers I of FIG. 3 and glucose oxidase co-deposited on an electrode.

FIG. 11 is a graphical representation of cyclic voltammograms of a film of redox polymers I of FIG. 3 and soybean peroxidase co-deposited on an electrode.

DESCRIPTION OF THE INVENTION

The present invention is generally related to the electrodeposition of redox polymers on electrodes of electrochemical systems. The redox polymers may be electrodeposited on a variety of electrodes, such as carbon or graphite working electrodes, examples of which include vitreous carbon electrodes, screen-printed carbon electrodes (SPEs), and hydrophilic ink-printed graphite electrodes, and such as gold or platinum electrodes. The electrodeposition of redox polymers according to the present invention is particularly applicable to the deposition of redox polymer films on microelectrodes.

Electrochemical System

An example of an electrochemical system or cell 10 is schematically shown in FIG. 1A. The system includes a working electrode 12, here, an SPE, which, merely by way of example, may have a hydrophilic working surface area of about 96 mm$^2$ that is screen- or ink-printed onto a substrate 18. The ink may be in the form of an ink droplet 14, such as a droplet of about 25 µL of hydrophilic ink. The working surface is typically confined by a hydrophobic border 16, here, a ring, that surrounds the hydrophilic ink, to separate the electroactive working surface from the non-electroactive surfaces on the substrate.

The working electrode 12 is connected to a contact pad 22, by way of a conducting line 20 formed on the substrate. The contact pad 22 facilitates the application of a potential to the working electrode via an electrical connection 24. The conducting line may be insulated from exposure, such as exposure to oligonucleotides, by a suitable overlayer (not shown). The working electrode 12 is operably connected a counter electrode 26, such as a platinum electrode, and a reference electrode 28, such as an Ag/AgCl reference electrode, as shown. These counter and reference electrodes 26 and 28 may be present in an electrolytic solution (not shown) that surrounds the substrate 18, or may be part of the substrate 18.

The electrochemical system 10 may be part of an array 40 of similar electrochemical systems, as schematically shown in FIG. 1B. In such an array 40, it is not necessary for each working electrode 12 to have a dedicated counter electrode 26 or reference electrode 28, as shown, as the same counter electrode or reference electrode can serve multiple working electrodes of the array. In the array 40 of elctrochemical systems 10 shown in FIG. 1B, the working electrodes 12 may be microelectrodes, such as microelectrodes having a working surface area of about 1.8 mm$^2$, for example, formed by ink droplets of about 15 µL. The electrodeposition of redox polymer films, as described herein, is particularly applicable to microelectrodes of a multi-sensor array, such as that of FIG. 1B, although the electrodeposition of redox polymer films is applicable to a wide variety of electrodes.

Electrodeposition involves the crosslinking of a redox polymer and proceeds when a redox polymer film is adsorbed on the electrode. The greater the coverage by such a film the faster the electrodeposition. When the redox polymer is a polycation, its deposition is enhanced by incorporation of ionizable OH functions, such as those of carboxylic acids or phenols, in or at the carbon surface. These functions can be incorporated, for example, by oxidizing the surface. The surface can be oxidized, for example, by exposing the electrode surface to a gaseous oxygen plasma or by applying an oxidizing potential to the electrode while it is immersed in an electrolytic solution. Further by way of example, when the electrode is formed of small graphite particles, the edges of their van der Waals planes spontaneously react with oxygen in humid air to add OH functions.

Thus, according to the present invention, an electrode on which it is desired to deposit a redox polymer film may or may not need to be prepared, such as polished, rinsed or cleaned, and oxidized prior to the electrodeposition. Various electrode surface preparations are set forth in the Examples herein. Where pre-oxidation is desired, the electrode surface may be oxidized in a variety of ways, for example, naturally, such as by the exposure of graphite planes at the surface of a graphite electrode to air; induced by exposure of the electrode to a plasma, such as by the exposure of a vitreous carbon electrode to an oxidizing plasma; induced by electrochemical means, such as by electrooxidization of a vitreous carbon electrode; or accomplished by other means.

Electrodeposition of Redox Polymers and Co-Electrodeposition of Redox Enzymes

According to the present invention, redox polymers are deposited as a film on a surface of a working electrode 12 or on the surfaces of multiple working electrodes 12, such as those in an array 40. Typically, the films are not deposited on the substrate surface beyond the working surface of the working electrode, or between the working electrodes of multiple working electrodes in an array, so that electroactive and non-electroactive portions of the electrochemical cell or cells are isolated from one another.

Generally, electron-conducting redox polymers are electrodeposited by the formation of metallic bonds and hole-conducting redox polymers are electrodeposited upon the formation of covalent bonds. The deposited redox polymers generally provide for adequate transport of electrons or holes to and from the working electrode 12, when the redox polymer includes active redox functional groups that are mobile. By way of illustration, electron exchange between mobile segments of a hydrated redox polymer of an electrodeposited redox polymer film 50, in various stages 52, 54 and 56, is shown in FIG. 2. When the polymer is in a hydrated state 52, segments of the polymer, represented by ovals linked to the polymer backbone, are mobile and randomly collide. When a mobile reduced segment, represented by "e$^-$"-labelled oval, and a mobile oxidized segment, represented by an unlabelled oval, are within a distance δ of one another, as shown in state 54, an electron is transferred, as shown in state 56. For further details, see, for example, J. M. Saveant, *J. Electroanal. Chem. Interfacial Electrochem.* 1988, 242, 1–21; J. M. Saveant, *J. Phys. Chem.* 1988, 92, 4526–32; P. Andrieux, J. M. Saveant, *J. Phys. Chem.* 1988, 92, 6761–7; M. E. G. Lyons, H. G. Fay, T. McCabe, J. Corish, J. G. Vos, A. J. Kelly, *J. Chem. Soc., Faraday Trans.* 1990, 86, 2905–10; F. C. Anson, D. N. Blauch, J. M. Saveant, C. F. Shu, *J. Am. Chem. Soc.* 1991, 113, 1922–32; O. Haas, J. Rudnicki, F. R. McLarnon, E. J. Cairns, *J. Chem. Soc., Faraday Trans.* 1991, 87, 939–45; M. F. Mathias, O. Haas, *J. Phys. Chem.* 1992, 96, 3174–82; Aoki, A. Heller, *J. Phys. Chem.* 1993, 97, 11014–19; and Aoki, R. Rajagopalan, A. Heller, *J. Phys. Chem.* 1995, 99, 5102–5110.

An example of a hydrated redox polymer film, as just described, is a redox polymer hydrogel. Generally, a redox polymer hydrogel is formed upon the immersion of a redox polymer film in an aqueous solution. The redox hydrogel typically contains at least about 10% of water, such that water-soluble molecules typically permeate the redox hydrogel rapidly. It is believed that the redox hydrogel provides for transport of electrons generally as described in relation to FIG. 2. By way of example, electron conduction in the redox hydrogel is believed to occur through electron exchange between polymer segments that, being tethered, do not leach out from the hydrogel, but are nevertheless mobile within a limited, small radius. In applications in which a detection marker is incorporated into or hybridized with the redox polymer film or hydrogel, as described herein, the hydrogel provides for transport of electrons between the electrode and the detection marker.

According to the present invention, a particularly useful redox polymer comprises a redox species coordinatively or covalently bound to a polymer. Preferred redox species exchange electrons rapidly between one another and the working electrode so that the redox complexes can be rapidly oxidized or reduced, and are coordinatively or covalently bound to the polymer. Generally, the redox species comprise transition metals of Group VIII of the Periodic Table, such as osmium or ruthenium, and preferably, osmium. Thus, the redox complexes are transition metal complexes, most preferably osmium (Os2+/3+) complexes.

The redox polymer also comprises a labile ligand that is linked to the redox complex, preferably at its inner coordination sphere. Preferably, this ligand is a weakly coordinating ligand. It is also preferred that the labile ligand be anionic. Examples of suitable labile ligands include halide, pseudohalide, such as cyanate or thiocyanate, and perchlorate ligands, a preferred example being a chloride ligand. One or more nitrogen-containing ligands, such as a heterocyclic nitrogen-containing ligand, may also be linked to the redox complex. Merely by way of example, a suitable nitrogen-containing ligand is a pyridine-containing ligand, such as 2,2'-bipyridine (bpy), or a imidazole-containing ligand, such as 2,2'-biimidazole, or a derivative thereof.

The redox polymer comprises a strongly coordinating ligand that is linked to the polymer backbone. Preferably, this ligand, while being strongly coordinating, is not coordinated in the redox polymer prior to electrodeposition. The strongly coordinating ligand is preferably a nitrogen-containing ligand, such as an amine-, a pyridine-, or an imidazole-containing ligand, most preferably one of the latter two heterocyclic ligands, or derivatives thereof.

Most preferably, the redox polymer comprises an osmium complex, a labile chloride ligand linked to the inner coordination sphere of the complex, and an uncoordinated, yet strongly coordinating, pyridine- or imidazole-containing ligand linked to the polymer backbone. While various and preferred redox polymers, and redox polymer constituents, are described herein, it is contemplated that a wide variety of redox polymers, including those now known and those yet to be appreciated or identified, may be electrodeposited according to the present invention.

Suitable polymers for complexation with the redox species include polymers and co-polymers of poly(1-vinylimidazole) (PVI), poly(4-vinylimidazole) (PVI), poly(N-vinylimidazole) (PVI), poly(4-vinylpyridine) (PVP), and imidazole- or pyridine-modified poly-(acrylamide) (PAA). Suitable copolymer substitutents of poly(1-vinylimidazole) include acrylonitrile, acrylamide, acrylhydrazide, and substituted or quaternized N-vinylimidazole. The transition metal complexes coordinatively or covalently bind with the imidazole or pyridine groups of the polymer. Preferred polymers for coordinative-bonding have nitrogen-containing heterocycles, such as pyridine, imidazole, or derivatives thereof, capable of binding as ligands to the redox species to form redox polymers. For additional information regarding redox polymers, see, for example, U.S. Pat. Nos. 5,264,104; 5,356,786; 5,262,035; 5,320,725; and 5,665,222; and U.S. Patent Application Publication No. US 2002/0081588 A1.

Preferably, redox polymers suitable for electrodeposition according to the present invention have molecular weights from about $10^4$ about $10^6$ Daltons. Generally, between about ¼ and ⅕ backbone-constituting mers in the redox polymers are modified with redox functions.

The electrodeposition of hydrated redox polymers according to the present invention results in the formation of coordinative bonds, which crosslink the chains of the polymers. An exemplary redox polymer comprises a cationic transition metal complex, preferably an osmium complex, such as an $Os^{2+/3+}$ complex, coordinatively bound to a backbone of the polymer; an anionic ligand, preferably a weakly coordinating anion, such as a chloride ion ($Cl^-$), in an inner coordination sphere of the complex; and an uncoordinated, strongly coordinating ligand, preferably a pyridine or an imidazole ligand, bound to the backbone of the polymer. When such redox polymers, typically provided in an aqueous solution, are adsorbed on an electrode and electroreduced or electrooxidized, the weakly coordinating, anionic ligands and the uncoordinated, but strongly coordinating ligands, of the redox polymers undergo exchange, resulting in an electrodeposited, crosslinked redox polymer film. By way of example, when osmium complex-containing redox polymers are adsorbed on an electrode and osmium is electroreduced from $Os^{3+}$ to $Os^{2+}$, the coulombic component of the binding energy of the osmium complex is reduced, such that the weakly coordinating anions, such as labile chloride anions, in the inner coordination spheres of the osmium complexes, undergo exchange with more strongly coordinating ligands, such as pyridine or imidazole ligands, in the backbones of neighboring polymers.

This crosslinking ligand exchange may occur within a redox polymer, for example, when the exchange occurs in the aqueous redox polymer solution, or when the surface coverage by the precursor polymers is low. The crosslinking ligand exchange may also, or alternatively, occur between multiple redox polymers, for example, when the surface coverage by the precursor polymers is high. That is, when the precursor polymers do not densely cover the surface, the likelihood of finding neighboring polymer chains at distances short enough to exchange ligands is generally small, while when the coverage is more dense, this likelihood is increased. Typically, adequate exchange of ligands, and thus, adequate electrodeposition, occurs when the surface coverage by the precursor redox polymer is sufficiently high, such as at least about $10^{12}$, or at least about $5 \times 10^{12}$, complex centers per $cm^2$ of true surface area. Here, true surface area, as opposed to geometrical surface area, takes into account surface features, such as the roughness of the surface, which may be represented by a roughness factor that is a ratio of true surface area/geometric surface area. The true surface area may, and most often does, differ from the geometric surface, and sometimes substantially, such as 20-fold higher when the surface is somewhat rough or irregular. Examples of sufficient surface coverage are at least about $4 \times 10^{13}$ complex centers per $cm^2$ of true, surface, area, at the site of electrodeposition, preferably, at least about $7 \times 10^{13}$ complex centers per $cm^2$, and most preferably, at least about $1.1 \times 10^{14}$ complex centers per $cm^2$, as demonstrated in an Example set forth herein.

Thus, generally, ligand exchange that leads to the crosslinking of redox polymers occurs when transition-metal redox centers are electroreduced or electrooxidized, preferably electroreduced, and the surface density of adsorbed redox polymers is high. In a particular example, the surface density of polycationic redox centers adsorbed on a vitreous carbon electrode may be modulated, preferably increased, by oxidizing the surface of the electrode prior to adsorption. In this example, oxidation of the surface of the carbon electrode adds carboxylate and phenolate functions capable of binding with the polycations of the redox centers, such that adsorption of the redox centers is increased. See, for example, Y. Yang, Z. G. Lin, *J. Appl. Electrochem.* 1995, 25, 259–66. Generally, the rate of crosslinking by ligand exchange increases both with the surface density of the chain providing the inner-coordination-sphere ligand and that of the chain providing the polymer-backbone ligand, such that it scales superlinearly with the surface density of the adsorbed polymer. At high surface coverage, crosslinking is expected to be very rapid and at low coverage it is expected to be negligible.

Examples of redox polymers suitable for electrodeposition according to the present invention are represented by structures I, II, III and V of FIG. 3, as further described in relation to the Examples herein. Structures for comparative redox polymers IV and VI are also shown. Generally, the values for l, m and n (for structures I and II) or m and n (for structures III–VI) appearing in these structures are positive numbers. Suitable approximate values for l, m, and n for structures I–VI are set forth in Table 1 below.

TABLE 1

Values for l, m, and n for Redox Polymer Structures I–VI of FIG. 3

| Structure | l-Value | m-Value | n-Value |
|---|---|---|---|
| I | 5–10 or 5–20 | 1–3 | 70–90 |
| II | 5–10 or 5–20 | 70–90 | 3–10 |
| III | | 5–20 | 80–95 |
| IV | | 1–2 | 10–20 |
| V | | 5–20 | 80–95 |
| VI | | 1–2 | 10–20 |

The water-soluble redox polymers I, II, III and V are reversibly adsorbed in a sufficient amount on the working surface of the electrode and then irreversibly crosslinked via electroreduction or electrooxidation, as described above, and thus, electrodeposited as a redox polymer film on the working surface of the electrode. The resulting film conducts electrons when it is hydrated and the redox segments of its polymer components, while being tethered to the crosslinked polymer, are mobile enough to collide, as discussed above in relation to FIG. 2.

The electrodeposition is relatively rapid, occurring in approximately 200 seconds, and may proceed at up to about 80° C., or up to about 40° C., in an aqueous solution having a pH of from about 4 to about 9. Because the redox polymer crosslinking may occur under mild conditions, coordinative function-comprising biological macromolecules, such as amine-comprising proteins, for example, enzymes, or amine-functionalized nucleic acids, dissolved in the aqueous solution may be co-electrodeposited without becoming denatured. When an enzyme is present, for example, the electrodeposition preferably proceeds at up to about 40° C., most preferably at about room temperature or about 25° C., in an aqueous solution of approximately neutral pH, such as from about 6–8, and most preferably at about 7.0±0.3. Suitable enzymes for co-electrodeposition include those having transition metal-coordinating amine or heterocyclic nitrogen functions. Examples of suitable enzymes include those having transition metal-coordinating, such as osmium-coordinating, lysine, histidine and/or arginine functions. Further examples include redox enzymes such as various oxidases, such as glucose oxidase, various peroxidases, such as horseradish peroxidase (HRP) and soybean peroxidase (SBP), and copper enzymes, such as laccases and bilirubin oxidases, the copper enzymes preferably having four copper ions in their active units.

An electrode irreversibly electrodeposited with a redox polymer film and a redox enzyme, as described above, may be referred to as a "wired-enzyme electrode." A substrate of a co-deposited enzyme may be electrocatalytically oxidized or reduced on such a wired-enzyme electrode. See, for example, A. Heller, *J. Phys. Chem.* 1992, 96, 3579–3587; and R. Rajagopalan, A. Heller, Electrical 'Wiring' of Glucose Oxidase in Electron Conducting Hydrogels, pp. 241–254 in *Molecular Electronics*, (Eds. J. Jortner and M. Ratner) Blackwell Science, 1997. Examples of such substrates include glucose, for example, when the enzyme is glucose oxidase; hydrogen peroxide, for example, when the enzyme is a peroxidase; and oxygen, for example, when the enzyme is a copper enzyme, such as a laccase or a bilirubin oxidase.

Applications for Electrodes with Electrodeposited Redox Polymer Films

A particularly useful application of an electrode having a redox polymer film electrodeposited on its surface is now described. This application is particularly useful when an array of such electrodes is used. The array is preferably an array of screen-printed electrodes (SPEs), such as that described above in relation to FIG. 1B, which array may be mass manufactured by screen-printing hydrophilic carbon inks on polyester sheets, for example. Such arrays may be employed as electrochemical biosensors for monitoring, detecting or measuring various analytes in a sample of interest. An exemplary application is the use of such an array as an assay for detecting the presence of an oligonucleotide sequence in a sample and/or quantifying that sequence.

In this application, working electrodes of the above-described array, one of which 60 is schematically shown in FIG. 4, are electrodeposited with a redox polymer film or hydrogel 64, described above, by applying a negative potential. At the same time, or thereafter, at least one oligonucleotide 68 having a terminal amine, sometimes referred to as a capture probe or capture sequence, is incorporated into the redox polymer film, as shown in part A of FIG. 4. This incorporation generally involves the formation of a coordinative bond between the terminal amine of the capture sequence 68 and the transition metal complex of the redox polymer film 64. The incorporation process is preferably irreversible, such that a stable working assay is obtained.

When the assay is used to detect a target oligonucleotide or analyte 72, the working electrode 60 is exposed to a hybridizing solution containing the analyte to hybridize the analyte with the film-incorporated oligonucleotide 68, and thereby, capture the analyte, as schematically shown in part B of FIG. 4. Thereafter, the working electrode 60 is exposed to a hybridizing solution containing an enzyme-labeled oligonucleotide 76 (here, an HRP-labeled oligonucleotide is shown, for example), sometimes referred to as a detection probe or marker, or a detection sequence, to hybridize the analyte 72 with the enzyme-labeled oligonucleotide 76, as schematically shown in part C of FIG. 4. Upon this hybridization, the enzyme-labeled oligonucleotide 76 and the redox polymer film or hydrogel 64 are in electrical communication. Thus, as described previously, the redox polymer hydrogel 64 provides for the transport of electrons between the detection marker and the electrode, allowing for the detection of current at the electrode.

The enzyme 80 (here, HRP is shown, for example) of the enzyme-labeled oligonucleotide 76 serves as an electrocatalyst for oxidization or reduction of a substrate 84 (here, $H_2O_2$ is shown, for example) of the enzyme on the working electrode 60, as schematically shown in part D of FIG. 4. When such oxidization or reduction occurs, as schematically shown the various arrow-labeled portions of part D of FIG. 4, current flowing from the oxidization or reduction flows from the enzyme 76 to the redox polymer film or hydrogel 64 (here, an $Os^{2+/3+}$-containing redox polymer is shown, for example) for detection at the working electrode 60. The detection of this current indicates the presence of the target oligonucleotide 72.

A schematic illustration of the assay electrode, prior to optimization with a second layer of the redox polymer, is schematically shown in FIG. 5A. In this pre-optimized assay, for example, an electrode 90 is electrodeposited with a redox polymer film 94, a capture probe 98 is incorporated into the film, and an enzyme-labeled detection probe 102 is hybridized with the film. As depicted in FIG. 5A, the enzymes 104 of the detection probe 102 are somewhat remote from, or appear to be expelled from, the redox polymer-core electrodeposited film. It is believed that the enzyme (a polyanionic enzyme in the case of HRP, for example) is repelled by the DNA-loaded redox polymer, and thus, expelled from the redox polymer core, such that electron transfer from the redox polymer to the enzyme is reduced. That is, as the terminal enzymes 104 are located at the ends of rod-like sequences of the detection probe 102, which may be quite long, they may not be close enough to the transition metal 92 (such as $Os^{2+/3+}$ redox centers, for example) to accept electrons from these centers, and thus, fully participate in the electrocatalyzed reduction of the substrate (such as hydrogen peroxide, for example) of the enzyme.

It is believed that when a second layer 106 of redox polymer is electrodeposited on the electrode 90, as schematically shown in the optimized assay of FIG. 5B, the rod-like sequences of the detection probes 102 become more or less buried in the redox polymer, such that better contact is established between the redox centers 92 of the electrodeposited film and the enzymes 104, such that electrochemical communication or electron transfer therebetween is improved.

Optimization of the assay revealed additional advantages in the selection of the redox polymer used in producing the sandwich assay. More particularly, it was found that a poly(4-vinylpyridine)-co-acrylamide-containing redox polymer may outperform a poly(N-vinyl-imidazole)-co-acrylamide-containing redox polymer in a sandwich-type assay in terms of reducing noise from non-enzymatically-catalyzed electrochemical reactions taking place in the assay.

Thus, according to the present invention, sandwich-type amperometric assays of oligonucleotides may be performed using mass-manufacturable carbon electrodes, such as those screen-printed on polyester sheets as described above. In an optimization of these electrodes for use in assays, as set forth in an Example herein, it was determined that another redox polymer film may be advantageously electrodeposited on the assay following incorporation of the capture sequence in the initial redox polymer film. This additional layer of redox polymer film may increase the contact between the redox centers of the electrodeposited film and the enzyme of the enzyme-labeled oligonucleotide, as discussed below, and thus, improve the detection capability of the assay. Additional advantages were found in the selection of the redox polymer used in producing electrodes for the sandwich-type assay, as also set forth in one of the Examples set forth below.

EXAMPLES

Electrochemical Testing in Examples 1–5

In Examples 1–5 described herein, electrochemical testing was carried out using a Model 832 electrochemical detector from CH Instruments of Austin, Tex. The three-electrode electrochemical cell had a glassy carbon working electrode, a micro-Ag/AgCl reference electrode from Bioanalytical Systems of West Lafayette, Ind., and a platinum-foil counter electrode. The electrodes were placed in a homemade, 1.0 mL-volume electrochemical cell. An Analytical Rotator from Pine Instrument Company of Grove City, Pa. was used to control mass transport within the cell. All potentials set forth in Examples 1–5 are relative to the Ag/AgCl (3M NaCl) reference electrode, unless stated otherwise.

Example 1

Synthesis of Redox Polymers and Electrode Preparation

The structures of six different redox polymers I–VI synthesized for this Example are shown in FIG. 3. Structures I, II, III, and V represent redox polymers according to the present invention, while structures IV and VI represent comparative redox polymers. In the syntheses of these six redox polymers, $[Os(bpy)_2Cl_2]$ (where bpy is 2,2'-bipyridine), synthesized from $K_2OsCl_6$ by the procedure of Lay et al., was used. (See Lay et al.: P. A. Lay, A. M. Sargeson, H. Taube, *Inorg. Chem.* 1986, 24, 291–306.)

The six redox polymers were synthesized as previously described in the literature, as set forth below. In the synthesis of redox polymer I, poly(4-vinyl-imidazole-co-acrylamide) was partially imidazole-complexed with $[Os(bpy)_2Cl]^{+/2+}$, as described in T. de Lumley-Woodyear, P. Rocca, J. Lindsay, Y. Dror, A. Freeman, A. Heller, *Anal. Chem.* 1995, 67, 1332–1338. In that of redox polymer II, poly(4-vinylpyridine) was partially complexed with $[Os(bpy)_2Cl]^{+/2+}$ and partially quaternized with 2-bromoethylamine (to increase its solubility in water), as described in B. A. Gregg, A. Heller, *J. Phys. Chem.*, 1991, 95, 15, 5970–5975.

In the synthesis of redox polymer III, poly(N-vinyl imidazole) was partially complexed with $[Os(4,4'-diamino-2,2'-bipyridine)_2Cl]^{+/2+}$, as described in G. Maerker, F. H. Case, *J. Am. Chem. Soc.*, 1958, 80, 2475 (Maerker et al.). 4,4'-dinitro-2,2'-bypyridine-N,N'-dioxide was prepared as described in S. Anderson, E. C. Constable, K. R. Seddon, E. T. Turp, J. E. Baggott, J. Pilling, *J. Chem. Soc., Dalton Trans.*, 1985, 2247; and G. Kenausis, C. Taylor, R. Rajagopalan, A. Heller, *J. Chem. Soc., Faraday Trans.*, 1996, 92, 4131 (Kenausis et al.). 4,4'-diamino-2,2'-bipyridine (da-bpy) was synthesized from 4,4'-dinitro-2,2'-bypyridine-N,N'-dioxide by modifying the procedure of Maerker et al. (above). $Os(da-bpy)_2Cl_2$ was prepared by (a) dissolving $(NH_4)_2OsCl_6$ and da-bpy in ethylene glycol in a 1:2 molar ration and refluxing the solution under argon for 1 hour to obtain about a 90% yield of $Os(da-bpy)_2Cl_2$, and (b) complexing the $Os(da-bpy)_2Cl_2$ with poly(1-vinylimidazole) (PVI) at a complex:mer molar ratio of 1:4, and purifying the resulting complex, as described in Kenausis et al. (above) and R. J. Forster, J. G. Vos, *Macromolecules*, 1990, 23, 4372.

In the synthesis of comparative redox polymer IV, poly (N-vinylimidazole) was partially complexed with $[Os(4,4'-dimethyl-2,2'-bipyridine)(terpyridine)]^{2+/3+}$, as described in S. C. Barton, H. H. Kim, G. Binyamin, Y. C. Zhang, A. Heller, *J. Am. Chem. Soc.* 2001, 123, 5802–5803. In that of redox polymer V, poly(N-vinylimidazole) was partially N-complexed with $[Os(bpy)_2Cl]^{+/2+}$, as described in T. J. Ohara, R. Rajagopalan, A. Heller, *Anal. Chem.* 1993, 65, 3512–3517. In the synthesis of redox polyrer VI, poly(N-vinylimidazole) was complexed with $[Os(bpy)(terpyridine)]^{2+/3+}$, also as described in S. C. Barton, H. H. Kim, G. Binyamin, Y. C. Zhang, A. Heller, *J. Am. Chem. Soc.* 2001, 123, 5802–5803.

In the electrodeposition of each one of the six redox polymers, the redox polymer was placed in an aqueous, phosphate-buffered saline solution (PBS solution), having a sodium chloride concentration of about 0.15 M, a phosphate concentration of about 0.02 M, and a pH of about 7.1, that was freshly prepared using de-ionized water. The electrodes targeted for electrodeposition were 3 mm-diameter vitreous carbon electrodes. These electrodes were polished with alumina, rinsed with de-ionized water, and cycled between about −0.4 V and about +0.8 V until the featureless voltammograms of sequential cycles were identical. In various electrodeposition tests, the vitreous carbon electrodes were pre-oxidized in an air plasma at a pressure of about 1 torr for about 5 minutes prior to the electrodeposition. In other electrodeposition tests, the vitreous carbon electrodes were pre-oxidized by electrooxidation of the electrode surfaces.

Electrodeposition was carried out, though not as rapidly, by exceptionally electrooxidation and electroreduction, merely by exposing the plasma-pre-oxidized, vitreous carbon electrodes to the aqueous, redox polymer solution and cycling the electrodes between about −150 mV and about +150 mV relative to the redox potential of the redox polymer. When the vitreous carbon electrodes were not pre-oxidized by exposure to a plasma, they had to be cycled to greater than about +0.4 V versus a standard calomel electrode (SCE), such as about +0.5V versus SCE, prior to applying the electrodeposition potential in order for electrodeposition to proceed. Electrodeposition was attempted for each of the six redox polymers, whereby redox polymers I–III and V having a labile ligand in the inner sphere of the osmium complexes were electrodeposited, while redox polymers IV and VI were not.

Example 2

Electrodeposition of Redox Polymers

In further electrodeposition experiments, electrodeposition of crosslinked films of redox polymers I–VI of FIG. 3 were attempted. Aqueous solutions comprising from about 0.5 to about 1.0 mg/mL of the subject redox polymer in a PBS solution (about 20 mM phosphate and about 0.1 M NaCl, at a pH of about 7.1) were prepared. In a 200-second electrodeposition process, the potential was stepped 50 times between −0.3 V, for about 2 seconds, and +0.8 V, for about 2 seconds. A train of these applied potentials is illustrated in FIG. 6 as a sequence of square waves. It was noted that the rate of deposition increased when the oxidizing potential was raised to +0.8 V.

In these experiments, the electrodepositions of redox polymers I, II, III and V resulted in irreversibly deposited redox polymer films. Attempts to electrodeposit the comparative redox polymers IV and VI were unsuccessful. These and other results (i.e., film stability, oxidation potential of the redox polymer solution, oxidation potential of the redox polymer film, redox center coverage of the electrode) of these experiments are shown in Table 2 below.

TABLE 2

Results for Electroposited Redox Polymers and Comparative Redox Polymers

| Redox Polymer | Deposition of Film | Stable Film | $E_{1/2, Solution}$ (mV) | $E_{1/2, Film}$ (mV) | Coverage ($\Gamma \times 10^{10}$ mol/cm$^2$) |
|---|---|---|---|---|---|
| I | Yes | Yes | −10 | 10 | 6.0 |
| II | Yes | Yes | 325 | 340 | 7.8 |
| III | Yes | Yes | −130 | −90 | 6.2 |
| IV | No | | 550 | | |
| V | Yes | Yes | −10 | 20 | 4.2 |
| VI | No | | 545 | | |

The comparative redox polymers IV and VI lacking mobile inner-sphere ligands were not electrodeposited, while the redox polymers I, II, III and V comprising inner-sphere anions were electrodeposited. Stable or persistent films were electrodeposited from solutions of those redox polymers I, II, III and V that had uncoordinated imidazole and pyrldine ligands and also $Os^{2+/3+}$-complexes with mobile inner-sphere ligands, as shown in the structures of FIG. 3.

Electrodeposition of redox polymers I, II, III, and V, according to the present invention, resulted in redox polymer films having a higher redox potential than that of the redox polymers in solution, as shown in Table 2. This result is as expected given the partial exchange of a weakly coordinating ligand and a more strongly coordinating ligand in the formation of these films.

For the successful electrodepositions of redox polymers I, II, III and V, cyclic voltammograms were integrated to determine the redox center coverage of the electrode surface. In the case of redox polymer I, the redox center coverage on the electrode surface was about $10^{-9}$ mol/cm$^2$. The redox center coverage results for redox polymers I, II, III and V are shown in Table 2.

Example 3

Electrochemical Characterization of Redox Polymer Films

Films of redox polymer I of FIG. 3 were electrodeposited on electrodes, as described in Example 2, where the reducing potential was fixed at about −0.3 V and the oxidizing potential was +0.80 V. Further such films were prepared, with the exception that while the reducing potential was fixed at about −0.3 V, as just described, the oxidizing potential varied in different electrodeposition processes, being set at about 0.40 V, 0.60 V, 0.70 V and 0.80 V, respectively. In each electro-deposition, a sequence of 50 square-wave potentials was applied to the electrodes.

Cyclic voltammograms of the deposited films of redox polymer I are graphically represented in FIG. 7, where the (•), (∗), (○) and (-) symbols correspond to the oxidizing potentials 0.40 V, 0.60 V, 0.70 V and 0.80 V, respectively. The scan rate was 100 mV/second. As shown, the cyclic voltammograms for these electrodeposited films are dependent on the oxidizing potential applied in the electrodeposition process, the relative magnitudes of the peak maxima and peak minima corresponding to the relative magnitudes of the oxidizing potentials employed. Thus, when the upper (most oxidizing) potential was increased stepwise from +0.4 V to +0.8 V, more redox polymer was electrodeposited in each cycle.

The waves of cyclic voltammograms of freshly electrode-posited films of redox polymer I exhibited pronounced tailing. The tailing disappeared upon repeated electrooxidation/reduction cycling of the films. After about 20 cycles, the persistent waves were narrow and had surface-immobilized, redox-couple characteristics. The peak heights increased linearly with the scan rate up to about 500 mV/s, and at slow scan rates, the peaks of the reduction and oxidation waves were separated by less than about 10 mV. Cyclic voltammograms of a fully annealed film of redox polymer I electrodeposited on vitreous carbon are graphically represented in FIG. 8, where the scan rates, from the innermost to the outermost waves, are about 10, 20, 50, 100 and 200 mV/s.

When redox polymer I was electrodeposited from an aqueous solution (about 0.5 mg/mL of redox polymer in a PBS solution), the thickness of the electroactive film increased linearly with the number of cycles in the first 50 cycles of about 2 seconds at a reducing potential, followed by about 2 seconds at an oxidizing potential. The thickness increased less, and non-linearly, between about 50 and about 200 cycles, and did not increase beyond about 200 cycles. As graphically demonstrated in FIG. 9, the peak current of the film similarly varied with the number of square-wave cycles applied, increasing substantially linearly for the first 100 or so cycles, increasing less, and non-linearly, between about 100 and about 200 cycles, and not increasing significantly or appreciably beyond about 200 cycles. Thus, in the first 100 cycles, the amount of redox polymer deposited in each cycle was about the same; between 100 and 200 cycles, the amount of polymer deposited in each cycle decreased incrementally as the cycle number increased; and beyond 200 cycles, there was little or no incremental change in the amount of polymer deposited in each cycle.

According to the present invention, the redox cycling may be varied to obtain a desirable film. Merely by way of example, cycling comprising anywhere from about 10 to about 200 redox cycles, or from about 50 to about 60 redox cycles, are suitable. Further, in the redox cycling, the periods of application of a negative or a positive potential may be varied. Thus, while this Example employed a 2-second period for both the negative and the positive potential applications, a period of from about 0.5 second to about 4 seconds, for example, may be used for each of the negative and the positive potential applications, and the periods for each need not be the same.

Example 4

Co-Electrodeposition of Redox Enzymes

In Examples 1–3 above, electrodepositions of redox polymer films were carried out under mild conditions, for example, by using an aqueous solution at about room temperature and approximately neutral pH. As previously discussed, these mild conditions are ideal for the co-deposition of enzymes, such as enzymes having osmium-coordinating lysine, histidine and/or arginine functions; oxidases, such as glucose oxidase (GOX); peroxidases, such as horseradish peroxidase (HRP) and soybean peroxidase (SBP); and copper-containing enzymes, such as laccases and bilirubin oxidases.

In this Example, aqueous solutions comprising redox polymers and enzymes having $Os^{2+/3+}$-coordinating lysine, histidine and arginine functions were used to co-electrodeposit the redox polymers and the enzymes on electrodes. Redox polymer I of FIG. 3 (at about 0.50 mg/mL), a redox enzyme (at about 0.50 mg/mL) selected from glucose oxidase (GOX), horseradish peroxidase (HRP), soybean peroxidase (SBP), and laccase, and a PBS solution (at about 0.15 M NaCl, about 0.02 M phosphate, a pH of about 7.1, freshly prepared with de-ionized water) were combined to produce an aqueous solution having a pH of about 7.2±0.1 at room temperature for each of the enzymes. The glucose oxidase (EC 1.1.3.4, Type X-S, from *Aspergillus niger*, 213 units/mg of solid) was purchased from Fluka (Fluka Chime AG, Buchs); the horseradish peroxidase (EC 1.11.1.1, Type VI, 330 units/mg) and the laccase (EC 1.10.3.2, 180 units/mg) were purchased from Sigma Chemical Co. (St. Louis, Mo.); and the soybean peroxidase (HP grade, 130 pyrogallol units/mg) was purchased from Enzymol International, Inc. The electrodes were 3 mm-diameter, vitreous carbon electrodes that were cycled to +0.8 V versus Ag/AgCl to oxidize their surfaces, and then cycled to a reducing potential of −0.4 V versus Ag/AgCl for electrodeposition by crosslinking.

Electrodeposition from the various solutions on electrodes according to the present invention resulted in electrocatalytic films on which substrates of the enzymes were selectively electrooxidized/reduced. Thus, glucose was electrooxidized on the electrodes by a film of redox polymer I and co-deposited GOX (I-GOX); hydrogen peroxide was electroreduced on the electrodes by a film of redox polymer I and co-deposited HRP (I-HRP) or SBP (I-SBP); and oxygen was electroreduced on electrodes by a film of redox polymer I and co-deposited laccase (I-LAC).

Cyclic voltammograms of the I-GOX-filmed and the I-SBP-filmed electrodes are graphically represented in FIGS. 10 and 11, respectively. In FIG. 10, the waves labeled with a (○) symbol represent exposure to a PBS solution lacking glucose, and the waves labeled with a (-) symbol represent exposure to a PBS solution having a glucose concentration of about 20 mM. In FIG. 9, the waves labeled (○) represent exposure to a PBS solution lacking hydrogen peroxide and the waves labeled (-) represent exposure to a PBS solution having a hydrogen peroxide concentration of about 1.0 mM. The PBS solutions just described were at a pH of about 7.1. The scan rate was 5 mV/second.

Like the pure redox polymer films, the redox polymer-enzyme films also had the characteristics of electrodes with fast, surface-bound redox couples. At scan rates up to about 100 mV/s, the separation of the peaks of the voltammetric electroreduction and electrooxidation waves was less than about 10 mV in the co-deposited electrodes. Practically no hysteresis was observed at a scan rate of about 10 mV/s, as shown in FIGS. 10 and 11.

Example 5

Redox Polymer Coverage at Electrode Surface

In this Example, three vitreous carbon electrodes were prepared for electrodeposition. A first, untreated electrode was polished with about 0.05 μm $Al_2O_3$ and then thoroughly cleaned in an ultrasonic bath. A second, plasma-treated electrode was similarly polished and cleaned, and then treated in an oxygen plasma for about 5 to about 10 minutes. A third, electrochemically treated, in this case, oxidized, electrode was similarly polished and cleaned, and then placed in a PBS solution (of about 0.14 M sodium chloride and about 20 mM phosphate, having a pH of about 7.2) and subjected to square-wave potential cycling (comprising 50 cycles) or to electrolysis at about +0.8 V versus SCE for about 5 to about 10 minutes.

Each of the electrodes was separately soaked in a redox polymer solution of a PAA-PVI-Os (at about 1.0 mg/mL), as depicted below, a copolymer of acrylamide and 1-vinylimidazole, in which the imidazole functions are complexed with $[Os(4,4'\text{-dimethyl-bpy})_2Cl]^{+/2+}$.

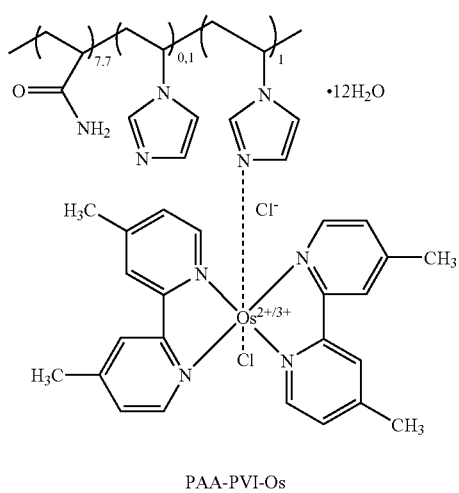

PAA-PVI-Os

For PAA-PVI-Os synthesis, see T. de Lumley-Woodyear, P. Rocca, J. Lindsay, Y. Dror, A. Freeman, A. Heller, *Anal.*

Chem. 1995, 67, 1332–1338. Each electrode was soaked in this solution for about 5 to about 10 minutes and then rinsed briefly with water.

For each of the electrodes, cyclic voltammograms were run at various scan rates in a blank PBS solution. The electrode was then rinsed and the cyclic voltammograms were run again to check stability. The current peaks of the voltammograms were then integrated to determine the charges, or the concentration of transition metal (here, $Os^{2+/3+}$) redox centers, at the electrode surfaces.

For each electrode, the stability was fairly good. The first, untreated electrode had a surface coverage of about $4.6 \times 10^{-11}$ to about $5.4 \times 10^{-11}$ mole/cm$^2$ (average of about $5.1 \times 10^{-11}$ mole/cm$^2$), and little or no appreciable deposition was observed. The second, plasma-treated electrode had a surface coverage of about $2.0 \times 10^{-10}$ to about $2.5 \times 10^{-10}$ mole/cm$^2$ (average of about $2.3 \times 10^{-10}$ mole/cm$^2$), and deposition of the redox polymer was observed. The average surface coverage for the second electrode corresponds to about $1.4 \times 10^{14}$ transition metal centers per square centimeter of true, not geometric, surface area. The third, electrochemically treated electrode had a surface coverage of about $1.7 \times 10^{-10}$ to about $2.2 \times 10^{-10}$ mole/cm$^2$ (average of about $2.0 \times 10^{-10}$ mole/cm$^2$), and deposition of the redox polymer was observed. The average surface coverage for the third electrode corresponds to about $1.2 \times 10^{14}$ transition metal centers per square centimeter of true surface area.

Based on this Example, surface coverage sufficient for electrodeposition of redox polymers is contemplated as being at least about $4 \times 10^{13}$, preferably at least about $7 \times 10^{13}$, and most preferably, at least about $1.1 \times 10^{14}$, transition metal centers per square centimeter of true surface area.

Results of Examples 1–5

The results of Examples 1–5 demonstrate that films of redox polymers, having either pyridine or imidazole functions in their backbone and mobile inner-sphere ligands in their $Os^{2+/3+}$-complex redox centers, are irreversibly electrodeposited by redox cycling. Neighboring imidazole-OsCl$^+$ or pyridine-OsCl$^+$ pairs exchange ligands thereby crosslinking the polymers. There are a few general characteristics that describe ligand exchange-based crosslinking and electrodeposition of redox polymers according to the present invention. These include electrodeposition of a redox polymer film from a redox polymer having transition metal complex-based redox centers that contain labile ligands in their inner coordination spheres; electrodeposition of a redox polymer film from a redox polymer that contains strongly coordinating, yet uncoordinated ligands; electrodeposition of redox polymer film on a surface that has a sufficient density or coverage of a redox polymer on its surface; and electrodeposition of a electron- or hole-conducting redox polymer film.

Example 6

Assays Using Electrodes with Electrodeposited Redox Polymer Films

An example of assays based on electrodes with electrodeposited redox polymer films is now described. See also, M. Dequaire, A. Heller, *Anal. Chem.*, 2002, 74, 4370–4377. The hybridizations of this Example were performed using a DIGI-BLOCK JR Laboratory Devices block heater from Sigma-Aldrich. The electrochemical measurements carried out in a Faraday cage with a Model 832A electrochemical detector (from CH Instruments of Austin, Tex.), interfaced with an OptiPlex Gxi computer (from Dell of Austin, Tex.).

Electrode Preparation

In this Example, experiments were performed using 3.6 mm-diameter, screen-printed carbon electrodes (SPEs), printed on a flexible polyester film with a homemade polystyrene-based ink, namely, a 2:3 mixture of polystyrene foam and graphite particles (2–15 μm, from Alfa Aesar of Wardhill, Mass.) in mesitylene. See O. Bagel, B. Limoges, B. Schöllhorn, D. Degrand, *Anal. Chem.* 1997, 69, 4688–4694. The SPEs were made hydrophilic upon a 90-second exposure to an air plasma at 0.5 torr.

In further experiments, the homemade ink was replaced by a commercially available carbon ink, namely, Electrodag 423SS from Acheson of Port Huron, Mich. An array of 12 SPEs, as depicted in FIG. 1B and described previously, was produced using 10–35 μL ink droplets. Hydrophobic rings were drawn around the SPEs to avoid the spreading of the droplets beyond the 1.5 or 3.6 mm-diameter working electrodes using a felt-tip pen containing hydrophobic ink (DAKO Pen, S 2002, from DAKO Corporation of Carpinteria, Calif.). The electrochemical cell formed in the confined droplet had a screen-printed carbon working electrode; a 0.9 mm-diameter, mechanical-pencil-carbon-lead (HB hardness) counter electrode or a 0.5 mm-diameter, platinum-wire counter electrode; and an Ag/AgCl reference microelectrode (3M KCl saturated with AgCl, from Cypress of Lawrence, Kans.), to which all potentials are referenced unless stated otherwise.

Redox Polymer Preparation

An electron-conducting redox polymer, namely, a 7:1 polymer of acrylamide and 1-vinylimidazole, the imidazole functions complexed with $[Os(4,4'\text{-dimethyl-bpy})_2Cl]^{+/2+}$, which copolymer may be referred to as PAA-PVI-Os, as depicted above in Example 5, was synthesized. (See T. de Lumley-Woodyear et al. reference cited in Example 5.)

Capture Sequence Preparation

Capture sequences, identified as $C_i$ in Table 3 below, where i=1 or 2, SEQ ID NO 1 and SEQ ID NO 3, respectively, were custom-prepared by Synthetic Genetics of San Diego, Calif. These capture sequences (SEQ ID NO 1 and SEQ ID NO 3) were modified with 5' amine-tenninated, 6-carbon spacers. For each capture sequence (SEQ ID NO 1 or SEQ ID NO 3), a 12-T spacer was appended on the 5' end of the capture sequence to allow for better hybridization.

Redox Polymer and Capture Sequence Solution Preparation

Solutions containing 1:7.5 weight ratio of one solution A, namely, 1 mg/mL PAA-PVI-Os in a PBS solution, and another solution B, namely, 0.1333 mg/mL of single-stranded oligonucleotides (SEQ ID NO 1 or SEQ ID NO 3) in a PBS solution, were prepared. These solutions are referred to as RP-CS Solutions below.

In the RP-CS Solutions, the ratio of redox polymers to capture sequences (SEQ ID NO 1 or SEQ ID NO 3) was maintained at about 8:1, to avoid precipitation of electrostatic adducts of the two. Alternatively, when it was desired to have a lower ratio, the redox polymers were electrodeposited from solution A first, and the capture sequences (SEQ ID NO 1 or SEQ ID NO 3) were then electrodeposited from solution B.

Target Sequence Preparation

Target sequences, identified as $T_2$, $T_2'$ and $T_2''$ in Table 3 below, where no prime indicates no mismatched bases, where one prime indicates one mismatched base (T), (and where two primes indicate two mismatched bases (C and A), SEQ ID NO 4, SEQ ID NO 5 and SEQ ID NO 6, respectively, were custom-prepared by Synthetic Genetics of San Diego, Calif. Hybridization buffer solutions containing the target sequences (SEQ ID NO 4, SEQ ID NO 5 and SEQ ID NO 6) were prepared. These solutions are referred to as HB-TS Solutions below.

Detection Sequence Preparation

Enzyme-labeled oligonucleotide detection sequences, identified as $D_i$ in Table 3 below, where i=1 or 2, SEQ ID NO 2 and SEQ ID NO 7, respectively, were custom-prepared by Synthetic Genetics of San Diego, Calif. $D_1$ (SEQ ID NO 2) and $D_2$ (SEQ ID NO 7) were 5'- and 3'-labeled with HRP, respectively. The HRP labels of these detection sequences (SEQ ID NO 2 and SEQ ID NO 7) were assayed, confirming that the activity of the probe-bound HRP on a molar basis did not differ from that of the pure HRP and that the specific activity of the HRP was $10^4$ units/mg. Hybridization buffer solutions containing the detection sequence (SEQ ID NO 2 or SEQ ID NO 7) (50 nM) in hybridization buffer were prepared.

Integration of voltammograms for film-layered, 1.5-diameter SPEs (hydrophilic ink, no plasma treatment) revealed that whether the films were deposited by poising the electrodes at a fixed potential or by redox cycling, the transition metal ($Os^{2+/3+}$) coverage on the surfaces of the electroactive electrodes was about the same. Further, whether the fixed potential was −0.2, −1.025, or −1.4 V, the coverage was about the same. The coverage was about $1.3\pm0.1\times10^{-10}$ mol/cm$^2$, with a standard deviation of about ±11% for a batch of 16 electrodes.

In a particular example, a redox polymer film (PAA-PVI-Os) and a single-stranded capture sequence, $C_1$ (SEQ ID NO 1), in a 15:1 weight ratio, were co-electrodeposited on 3.6 mm-diameter electrodes, and the resulting films (PAA-PVI-

TABLE 3

Oligonucleotide Sequences for Capture, Target, and Detection Probes

| Ref. No. | SEQ ID NO: | Sequence | % T |
|---|---|---|---|
| $C_1$ | 1 | TTT TTT TTT TTT GGG GGG GGG GGG GAG CAA AGG TAT TAA CTT TAC TCC C | 38.8 |
| $D_1$ | 2 | TTT TTT TTT TTG GGA GTA AAG TTA ATA CCT TTG CTC CCC CCC CCC CCC | |
| $C_2$ | 3 | TTT TTT TTT TTT CAC TTC ACT TTC TTT CCA AGA G | 58.8 |
| $T_2$ | 4 | AGG CAT AGG ACC CGT GTC CTC TTG GAA AGA AAG TGA AG | |
| $T_2'$ | 5 | AGG CAT AGG ACC CGT GTC CTC TTG GAA TGA AAG TGA AG | |
| $T_2''$ | 6 | AGG CAT AGG ACC CGT GTC CTC TCG GAA AGA AAG AGA AG | |
| $D_2$ | 7 | GAC ACG GGT CCT ATG CCT | |

Electrodeposition of Redox Polymer Films Containing Capture Sequences

Redox polymer films containing capture sequences (SEQ ID NO 1 or SEQ ID NO 3) were electrodeposited from RP-CS Solutions as now described. 15 μL aliquots of an RP-CS Solution were pipetted onto the SPEs and electrodepositions were carried out by applying a steady reducing potential, usually about −0.4 V to the electrodes for about 2 minutes.

In cases where the capture sequences (SEQ ID NO 1 or SEQ ID NO 3) had particularly high mol-fractions of T, or where a lower redox polymer to capture sequence ratio was desired, as described above, the redox polymer films described above were electrodeposited from solution A by applying 60 square-wave potential cycles of +0.8 V for 2 seconds and −0.3 V for 2 seconds, and separately and subsequently, the capture sequences (SEQ ID NO 1 or SEQ ID NO 3) described above were incorporated from solution B into the films by similar redox cycling.

The presence of the capture sequences (SEQ ID NO 1 or SEQ ID NO 3) in the films electrodeposited on the SPEs was confirmed. It was also noted that the activity of the electrodeposited film-layered electrodes did not change upon storage at 4° C. for two weeks.

A voltammogram for a film-layered, 3.6 mm-diameter SPE (via fixed potential of −1.4 V for 2 minutes) indicated a 107±2 mV redox potential for the film. The peaks of the voltammetric waves (at a 50 mV/s scan rate) were separated by ΔEp=35±2 mV, and integration of the waves yielded a faradaic charge of 1.4±0.1 μC for the reduction wave and 1.6±0.2 μC for the oxidation wave, corresponding to a transition metal ($Os^{2+/3+}$) coverage on the surface of the electroactive electrode of $1.6\pm0.1\times10^{-10}$ mol/cm$^2$. The standard deviation for the surface coverage was about ±9% for 20 electrodes from 5 random batches.

Os-$C_1$) were then hybridized with an enzyme-labeled (here, HRP-labeled) detection sequence, $D_1$ (SEQ ID NO 2), in a 25 μL droplet. Upon exposure to hydrogen peroxide, the HRP-labeled $D_1$ (SEQ ID NO 2) was detected at 5 nM, corresponding to 125 femtomoles of $D_1$ in the 25 μL droplet, with a signal to noise ratio of 6. When twelve, 1.5 mm-diameter electrodes of an array, such as that shown in FIG. 1B, were similarly prepared by a two-minute co-electrodeposition of the same redox polymner, PAA-PVI-Os, and the same capture sequence, $C_1$ (SEQ ID NO 1), from 15 μL droplets (at 1 mg/mL of PAA-PVI-Os), the resulting redox polymer films had 1.21±Coulombs/cm$^2$ of electroactive $Os^{2+/3+}$. Upon hybridization with the same HRP-labeled detection sequence, $D_1$ (SEQ ID NO 2), and exposure to hydrogen peroxide, the detection sequence was detected at 3 nM, corresponding to 75 femtomoles of $D_1$ (SEQ ID NO 2) in the 15 μL droplet, with a signal to noise ratio of 5.

Sandwich-Type Assay

Target sequences were hybridized with the capture sequences of the capture sequence-incorporated redox polymer films as now described. 25 μL aliquots of an HB-TS Solution were pipetted onto the film-covered SPEs, which were held at 53° C. for 15 minutes, then cooled and held at room temperature for 10 minutes, and then rinsed sequentially in 5 mL of washing buffer for 10 minutes and 5 mL hybridization buffer for 5 minutes. The SPEs were then incubated with 25 μL of a 50 nM solution of the detection sequence in hybridization buffer at 37° C. for 40 minutes, then cooled and held at room temperature for 10 minutes, and then rinsed. A 30 μL-droplet of a PBS solution was then applied to the SPE, the presence of the redox polymer was confirmed by cyclic voltammetry (at a scan rate of 5 mV/s), a 5 μL-droplet of hydrogen peroxide (1 mM) was then applied to the SPE, and the increase in the steady-state hydrogen peroxide electroreduction current was measured.

In a particular example, PAA-PVI-Os-C$_2$ (where C$_2$ corresponds to SEQ ID NO 3), a 20 hybridizing-base capture probe of a capture sequence-incorporated redox polymer film, was hybridized (at 53° C., for 15 minutes) with a target sequence, namely, a 38-base T$_2$ (SEQ ID NO 4) target in a 25 µL droplet. A detection probe, namely, an HRP-labeled, 18-base D$_2$ (SEQ ID NO 7) detection probe, was then hybridized with the target (SEQ ID NO 4). It was found that the optimal concentration of the detection probe (SEQ ID NO 7) was about 50 nM when the concentration of the target (SEQ ID NO 4) was about 10 nM. Upon exposure 16 mM hydrogen peroxide at ±0.2 V versus Ag/AgCl, the target T$_2$ (SEQ ID NO 4) was detected at a concentration of 200 pM, corresponding to 5 femtomoles of the target (SEQ ID NO 4) in the 25 µL droplet.

A voltammogram (at a 5 mV/s scan rate) for an electrode modified with the perfectly matched target T$_2$ (SEQ ID NO 4) gave a signal that was about twice that for an electrode modified with the singly-mismatched target T$_2$' (SEQ ID NO 5) and even greater relative to that for an electrode modified with the doubly-mismatched target T$_2$" (SEQ ID NO 6). Thus, sandwich-type assays using electrodeposited electrodes according to the present invention can be used to detect targets and to discriminate between perfectly matched targets and mismatched targets.

This Example demonstrates that sandwich-type amperometric assays of oligonucleotides may be performed using electrodeposited, mass-manufacturable carbon electrodes according to the present invention. Those skilled in the art will appreciate that the techniques exemplified here and shown throughout the specification will permit the preparation of sensors that can be manufactured in large quantities at relatively small cost, such that disposable sensors can be made. Such systems can include the electrode arrays shown herein, using, for example, printed electrodes, and the sensors can be formed into strips (and other shapes) that can be inserted into separate electronics (such as a hand-held or table-top analyzer) when used.

Example 7

Optimization of Assays Using Electrodeposited Electrodes

As demonstrated in Example 6, a 38-base DNA sequence (SEQ ID NO 4) was detected at a 20 pM concentration in 15–35 µL droplets by an electrochemical, enzyme-amplified, sandwich-type assay on a mass-manufacturable, screen-printed carbon electrode. The sandwich-type assay served as an electrocatalyst for the reduction of hydrogen peroxide to water at ±0.2 V versus Ag/AgCl. In optimizations of this assay, an approximately 20-fold improvement in detection sensitivity was realized, as described below.

More particularly, in an optimization of the assay, the poly(N-vinylimidazole)-co-acrylamide-containing redox polymer (PAA-PVI-Os) of Example 6 was replaced by a poly(4-vinylpyridine)-co-acrylamide-containing redox polymer (PAA-PVP-Os). This allowed the poising of the electrodes at a more oxidizing potential, which resulted in an approximately 5-fold reduction in noise, where noise refers to non-enzymatically-catalyzed electroreduction currents associated with dissolved oxygen and hydrogen peroxide.

In a further optimization of the assay, a second layer of the redox polymer was electrodeposited over the capture sequence (SEQ ID NO 3)-containing film. This resulted in an approximate doubling of the catalytic electroreduction current. In yet a further optimization of the assay, the capture-sequence (SEQ ID NO 3) coverage of the electrode surface was increased, which resulted in an approximate doubling of the current.

General Optimization Conditions

In these optimizations, the equipment used for hybridization and electrochemical detection was the same as that set forth in Example 6. Buffer salts and inorganic chemicals were purchased from Sigma of St. Louis, Mo., as were used as stated unless otherwise indicated. Phosphate buffer solution of pH 7.4 consisted of sodium phosphate (8 mM), potassium phosphate (2 mM), sodium chloride (140 mM), and potassium chloride (10 mM), and was purchased from Pierce of Rockford, Ill. The hybridization buffer (4.3 mM NaH2PO4,15.1 mM Na2HPO4, 500 mM NaCl, and 10 mM EDTA), washing buffer (4.3 mM NaH2PO4,15.1 mM Na2HPO4, 500 mM NaCl, and 0.5% Tween 20 from Aldrich of Milwaukee, Wis., and TE buffer (10 mM TRIS, mM EDTA, pH 7.7), and all other solutions were prepared using de-ionized water.

Electrode Preparation

In these optimizations, the electrode preparation was the same as that set forth in Example 6 for the 3.6 mm-diameter, screen-printed carbon electrodes (SPEs), printed on a flexible polyester film with the commercially available carbon ink, and pen-marked with hydrophobic ink.

Redox Polymer Preparation

An electron-conducting redox polymer, PAA-PVP-Os, was synthesized by dissolving 2.3 g of acrylamide (32 mmoles) and 0.5 mL of 4-vinylpyridine (4.6 mmoles) in a solution having a 1 to 1 volumetric ratio of acetone and water. The resulting solution was de-aerated by bubbling with argon for 30 minutes. 55 mg of ammonium persulfate and 60 µL of N,N,N',N'-tetramethyl-ethylenediamine in 10 mL mL of water were then added to the solution, which was then de-aerated for 10 minutes. The solution was then stirred at 40° C. for 13 hours, and then poured into 800 mL of acetone and stirred. Most of the solvent was evaporated and the residue was added to another 800 mL of acetone. Precipitate from the solution was collected, washed with acetone, and dried overnight under vacuum at room temperature. 120 mg of the resulting poly(4-vinylpyridine)-co-acrylamide (PAA-PVP) was then refluxed with 109 mg of Os(bpy)$_2$Cl$_2$ in 15 mL of ethylene glycol for 2 hours. The Os-complexed copolymer, PAA-PVP-Os, was precipitated in ether, re-dissolved in de-ionized water, and purified by ultra-filtration using a 10K cut-off membrane from Amicon of Beverly, Mass. The structure of the redox polymer, confirmed by NMR, is shown below.

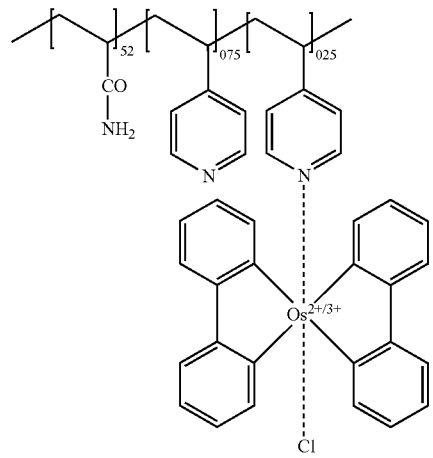

PAA-PVP-Os

Capture Sequence Preparation

Capture sequences, identified as $C_2$ (SEQ ID NO 3) in Table 3, were custom-prepared by Synthetic Genetics of San Diego, Calif. These capture sequences (SEQ ID NO 3) were modified with 5' amine-terminated, 6-carbon spacers. For each capture sequence (SEQ ID NO 3). a 12-T spacer was appended on the 5' end of the capture sequence (SEQ ID NO 3) to allow for better hybridization.

Redox Polymer Preparation

Solutions containing 1 mg/mL of PAA-PVP-Os and 18% by volume phosphate buffer were prepared.

Target Sequence Preparation

Target sequences, identified as $T_2$, $T_2'$ and $T_2''$ in Table 3 below, where no prime indicates no mismatched bases, where one prime indicates one mismatched base (T), and where two primes indicate two mismatched bases (C and A), SEQ ID NO 4, SEQ ID NO 5 and SEQ ID NO 6, respectively, were custom-prepared by Synthetic Genetics of San Diego, Calif. Hybridization buffer solutions containing the target sequences were prepared. These solutions are referred to as HB-TS Solutions below.

Detection Sequence Preparation

Enzyme-labeled oligonucleotide detection sequences, identified as $D_2$ (SEQ ID NO 7) in Table 3, were custom-prepared by Synthetic Genetics of San Diego, Calif. $D_2$ (SEQ ID NO 7) was 3'-labeled with HRP. The HRP labels of these detection sequences (SEQ ID NO 7) were assayed, confirming that the activity of the probe-bound HRP on a molar basis did not differ from that of the pure HRP and that the specific activity of the HRP was $10^4$ units/mg. Hybridization buffer solutions containing the detection sequence (SEQ ID NO 7) (50 nM) in hybridization buffer were prepared.

Electrodeposition of Redox Polymer Films and Attachment of Capture Sequences

Redox polymer films were electrodeposited on the electrodes from 25 μL aliquots of the redox polymer-phosphate buffer solution described above, by applying a potential of −1.4 V to the electrodes for 2 minutes. The electrodes were then rinsed thoroughly with de-ionized water and scanned between 0.1 and 0.5 mV to confirm the deposition.

Thereafter, 25 μL aliquots of a solution of the capture probes (SEQ ID NO 3) (2 μM) and a phosphate buffer were pipetted onto the SPEs and electrodepositions were carried out by applying a steady reducing potential of about −1.4 V to the electrodes for about 2 to about 20 minutes. The electrodes were then rinsed with water and voltammograms were run in the 0.1 V and 0.5 V versus Ag/AgCl region.

In some of the optimizations, a second layer of the redox polymer was electrodeposited, after the capture probes (SEQ ID NO 7) were incorporated in the first layer of the redox polymer as just described.

Sandwich-Type Assay

Target sequences (SEQ ID NO 4, SEQ ID NO 5, or SEQ NO 6) were hybridized with the capture sequences (SEQ ID NO 3) of the capture sequence-incorporated redox polymer films as now described. 30 μL aliquots of an HB-TS Solution were pipetted onto the film-covered SPEs, which were held at 53° C. for 15 minutes, then cooled and held at room temperature for 10 minutes, and then rinsed briefly in hybridization buffer. The SPEs were then incubated with 30 μL of a 50 nM solution of the detection sequence in hybridization buffer at 37° C. for 40 minutes, then cooled and held at room temperature for 10 minutes, and then rinsed sequentially in a washing buffer for 10 minutes and in a PBS solution for five minutes. A 30 μL-droplet of a hydrogen peroxide (0.2 mM) and PBS solution was then applied to the SPE, at room temperature, with the SPE poised at 0.2 V versus Ag/AgCl.

Voltammetric Characterization of a Modified Electrode

A voltammogram for a film-layered, 3.6 mm-diameter SPE (via fixed potential of −1.4 V for 2 minutes) indicated about a 0.28 V redox potential for the film, which remained unchanged upon exhaustive washing with water or PBS. Integration of the voltammetric waves yielded a faradaic charge of about 7.4 μC for the oxidation wave, corresponding to a transition metal ($Os^{2+/3+}$) coverage on the surface of the electroactive electrode of about $8 \times 10^{-10}$ mol/cm$^2$.

The adsorption and electrodeposition of the capture sequence $C_2$ (SEQ ID NO 3) on the redox film-layered electrode, decreased the segmental mobility of the redox polymers, and thus, decreased the diffusivity of electrons in the redox polymer film, as demonstrated in a voltammogram by broadened voltammetric waves having peak maxima and minima of lesser magnitude. Electrodeposition of a second redox polymer layer following attachment of the capture sequence (SEQ ID NO 3), as described above, lowered the resistance to electron diffusivity, as demonstrated in a voltammogram by a doubling the magnitude of the peak maxima and minima of the voltammetric waves relative to those associated with the electrodeposition of the single redox polymer layer as described above.

When the double-layer, capture sequence (SEQ ID NO 3)-incorporated redox polymer film was hybridized with the target sequences (SEQ ID NO 4) and detection sequences (SEQ ID NO 7), voltammogram showed a decrease in the magnitude of the peak maxima and peak minima of the voltammetric waves. This cyclic voltammogram was dependent on scan rate, with the peak separation increasing with increasing scan rate. This dependence is attributed to the rigidity of the polyanion-crosslinked polycationic film, which reduces the diffusivity of electrons.

Signal Detection

In sandwich-type assays using an electrode modified with PAA-PVP-Os-$C_2$ (where $C_2$ corresponds to SEQ ID NO 3), and further modified with the perfectly matched target $T_2$ (SEQ ID NO 4) (at 1 nM in the HB-TS Solution), a current of 245±9 nA was detected. In such assays using electrodes modified with PAA-PVP-Os-$C_2$ (where $C_2$ corresponds to SEQ ID NO 3), and further modified with the singly mismatched or doubly mismatched targets $T_2'$ (SEQ ID NO 5) and $T_2''$ (SEQ ID NO 6), respectively, much smaller currents of 80±3 nA and 36±2 nA, respectively, were detected. Thus, sandwich-type assays using electrodeposited electrodes according to the present invention readily discriminate between perfectly matched targets and mismatched targets.

Increase in Detection Signal

As described above, the capture sequences (SEQ ID NO 3) were electrodeposited by applying a fixed potential to the redox polymer film-layered electrodes for a period of from 2 to 20 minutes. It was found the signal currents from of sandwich-type assays increased by a factor of about 1.8 when the period used in the capture sequence (SEQ ID NO 3) electrodeposition was increased from 2 to 10 minutes. More particularly, it was found that the H2O2 electroreduction current observed after hybridization of the target (SEQ ID NO 4, SEQ ID NO 5, or SEQ ID NO 6) (at 1 nM) and the detection sequence (SEQ ID NO 7) (at 50 nM) increased from 60 nA to 108 nA when the period used in the capture sequence (SEQ ID NO 3) electrodeposition was increased from 2 to 10 minutes.

Reduction in Noise

As demonstrated in Example 6, in sandwich-type assays using an electrode that was modified with PAA-PVI-Os-$C_2$, the target $T_2$ (SEQ ID NO 4) was detected at a concentration of 200 pM when the electrode was exposed to hydrogen peroxide at +0.2 V versus Ag/AgCl. The redox potential of PAA-PVI-Os is about +0.10 versus Ag/AgCl.

In this optimization Example, the sandwich-type assays were performed using an electrode that was electrodeposited with modified with PAA-PVP-Os-$C_2$ (where $C_2$ corresponds to SEQ ID NO 3), so to detect the target $T_2$ (SEQ ID NO 4). However, as PAA-PVP-Os has a redox of about +0.28 V versus Ag/AgCl, which is higher than that of PAA-PVI-Os, it was determined that the electrodes modified with PAA-PVP-Os could be poised at a relatively higher or more oxidizing potential in the assay process. At a more oxidizing potential, background current, or noise, from non-enzymatically-catalyzed reductions of dissolved oxygen and hydrogen peroxide are reduced. For example, while background currents of about 40 nA are typical in assays conducted at a redox potential of about +0.10 V, the background current associated with an assay using the PAA-PVP-Os redox polymer and a redox potential of about +0.20 V was only about 8 nA. This result represents about a 5-fold improvement in the signal to noise ratio associated with these sandwich-type assays.

Sandwich-Type Assays Using Electrodes with One or Two Redox Polymer Layer(s)

As described above, a redox polymer layer was deposited on the electrodes, and subsequently, capture sequences (SEQ ID NO 3) were electrodeposited by applying a fixed potential to the redox polymer film-layered electrodes for a period of 20 minutes in some cases. In one experiment, half of these electrodes had another redox polymer layer subsequently deposited. Thereafter, each of the electrodes, whether singly or doubly layered, were hybridized with the target sequence $T_2$ (SEQ ID NO 4) for 30 minutes, the concentration of the target sequence (SEQ ID NO 4) being variable, at 20, 50, 100, 200, 400, 800 or 1000 pM, and subsequently hybridized with the detection sequence $D_2$ (SEQ ID NO 7) at 50 nM for 40 minutes. The $H_2O_2$ electroreduction currents associated with the modified electrodes were then measured.

The results of this experiment showed that the currents increased linearly with the concentration of the target sequence (SEQ ID NO 4), whether one layer or two layers of redox polymer were electrodeposited. The linear increase in current with target (SEQ ID NO 4) concentration indicates that the rate of the binding of the target to the film during the target hybridization process is controlled by the transport of the target to the film, not by the kinetics of the hybridization upon adsorption of the target. The best-fit line ($R^2$=0.91) obtained from the data for the "single-layer" electrodes is represented by the following Equation 1:

measured current (nA)=(0.116(nA/pM)×target concentration (pM))−0.7(nA).

The best-fit line ($R^2$=0.98) obtained from the data for the "double-layer" electrodes is represented by the following Equation 2:

measured current (nA)=(0.235(nA/pM)×target concentration (pM))+17.1(nA).

A comparison of the two equations demonstrates that the slope, which corresponds to the sensitivity of the assay, for the double-layer electrodes is about twice that for the single-layer electrodes. Thus, the double-layer electrodes are about twice as sensitive as the single-layer electrodes when used in sandwich-type assays.

Sandwich-Type Assays Using Electrodes with Two Redox Polymer Layers

Sixty-nine independent assays were carried out using the "double-layer" electrodes described above. In 40 of these assays, the target (SEQ ID NO 4) concentration was 50 pM or less. The actual current deviated, on average, from that predicted by Equation 2 above by ±6.8 nA, or by about 16%. In 10 assays at a target (SEQ ID NO 4) concentration of 10 pM, the measured current, on average, was 17±3 na; in 17 assays at a target (SEQ ID NO 4) concentration of 20 pM, the measured current, on average, was 20±4 nA; and in 13 assays at a target (SEQ ID NO 4) concentration of 50 pM, the measured current, on average, was 29±8 nA. When the intercept current of about 17 nA is subtracted from these average measured currents, the currents become 0±3 nA at 10 pM; 3±4 nA at 20 pM; and 12±8 nA 50 pM, respectively.

Thus, when using a "double-layer" electrode of this Example, one can detect a target (SEQ ID NO 4) concentration of 20 pM, which corresponds to 0.6 femtomoles of the target oligonucleotide (SEQ ID NO 4) in the 30 μL droplet. This compares favorably to the "single-layer" electrode of Example 6, wherein the target (SEQ ID NO 4) was detected at a concentration of 200 pM, corresponding to 5 femtomoles of the target (SEQ ID NO 4) in the 25 μL droplet.

This Example demonstrates that sandwich-type amperometric assays of oligonucleotides may be performed using electrodeposited, mass-manufacturable carbon electrodes according to the present invention, and particularly, such electrodes that have been optimized as described herein.

Thin films of transition metal complex-based redox polymers are electrodeposited on electrodes via application of fixed or cycled potential. When hydrated, an electrodeposited film conducts electrons by electron exchange between backbone-bound, but mobile, functional segments of its redox polymer constituents. These functional segments, or redox complexes, have labile ligands, such as chloride anions, for example, in their inner coordination spheres. The backbones of the redox polymers have strongly coordinating ligands, such as pyridine- or imidazole-containing functions, for example, which are generally not coordinated prior to deposition. Electrodeposition results from coordinative crosslinking by exchange of labile ligands and strongly coordinating ligands between polymer chains, provided sufficient functional segments of the redox polymers are present at the electrode surface. When a biological macromolecule or protein, such as a redox enzyme, is added to the solution from which the redox polymer is electrodeposited, it is co-electrodeposited on the electrode surface. When the co-deposited film contains redox enzymes, for example, the modified electrode may be used to catalyze the electrooxidation or electroreduction of substrates of the enzymes. Electrodes modified according to the invention also have application in chemical or biological assays.

Various references and publications have been identified herein, each of which is incorporated herein in its entirety by this reference. Various aspects and features of the present invention have been explained or described in relation to beliefs or theories, although it will be understood that the invention is not bound to any particular belief or theory. Various modifications, processes, as well as numerous structures to which the present invention may be applicable will be readily apparent to those of skill in the art to which the present invention is directed upon review of the specification. Although the various aspects and features of the present invention have been described with respect to various embodiments and specific examples herein, it will be understood that the invention is entitled to protection within the full scope of the appended claims.

SEQUENCE LISTING

160> NUMBER OF SEQ ID NOS: 7

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1
tttttttttt ttggggggggg ggggggagcaa aggtattaac tttactccc         49

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 2
tttttttttt tgggagtaaa gttaatacct tgctcccccc cccccccc           48

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 3
tttttttttt ttcacttcac tttctttcca agag                          34

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 4
aggcatagga cccgtgtcct cttggaaaga aagtgaag                      38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 5
aggcatagga cccgtgtcct cttggaatga aagtgaag                      38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 6

```
aggcatagga cccgtgtcct ctcggaaaga aagagaag                              38

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gacacgggtc ctatgcct                                                    18
```

The invention claimed is:

1. Method of modifying an electrode surface, comprising:
providing an electrode surface;
providing redox polymers at the electrode surface, each redox polymer comprising a complex of a transition metal; a first ligand of the complex; and a second ligand; the providing redox polymers providing sufficient complex centers at at least a portion of the electrode surface for electrodeposition of the redox polymers; and
electrodepositing the redox polymers to form a redox polymer film on at least the portion of the electrode surface via application of a potential or at least one cycle of varied potential, the electrodepositing comprising coordinative crosslinking of the first ligand of a first redox polymer with the second ligand of the first redox polymer or the second ligand of a second redox polymer.

2. The method of claim 1, wherein the electrode surface comprises a material selected from carbon, gold and platinum.

3. The method of claim 1, wherein the electrode surface comprises graphite.

4. The method of claim 1, wherein the electrode surface is oxidized.

5. The method of claim 1, wherein the electrode is a microelectrode.

6. The method of claim 1, wherein the electrode is a screen-printed electrode.

7. The method of claim 6, wherein the screen-printed electrode is printed with hydrophilic ink.

8. The method of claim 6, wherein the portion of the screen-printed electrode is confined by hydrophobic ink.

9. The method of claim 1, wherein electrodepositing the redox polymers is such that the redox polymers are deposited only on the portion of the electrode surface.

10. The method of claim 1, wherein only the portion of the electrode surface is electroactive.

11. The method of claim 1, wherein providing redox polymers comprises providing hydrated redox polymers.

12. The method of claim 1, wherein providing redox polymers comprises providing redox polymers via an aqueous solution.

13. The method of claim 12, wherein a pH of the aqueous solution is from about 4 to about 9.

14. The method of claim 12, wherein a pH of the aqueous solution is from about 6 to about 8.

15. The method of claim 12, wherein a temperature of the aqueous solution is up to about 80° C.

16. The method of claim 12, wherein a temperature of the aqueous solution is up to about 40° C.

17. The method of claim 12, wherein the aqueous solution comprises a redox enzyme.

18. The method of claim 1, wherein providing redox polymers is such that at least about $4 \times 10^{13}$ complex centers per square centimeter are present at at least the portion of the electrode surface.

19. The method of claim 1, wherein providing redox polymers is such that at least about $7 \times 10^{13}$ complex centers per square centimeter are present at at least the portion of the electrode surface.

20. The method of claim 1, wherein providing redox polymers is such that at least about $1.1 \times 10^{14}$ complex centers per square centimeter are present at at least the portion of the electrode surface.

21. The method of claim 1, wherein the redox polymers are selected from redox polymers:

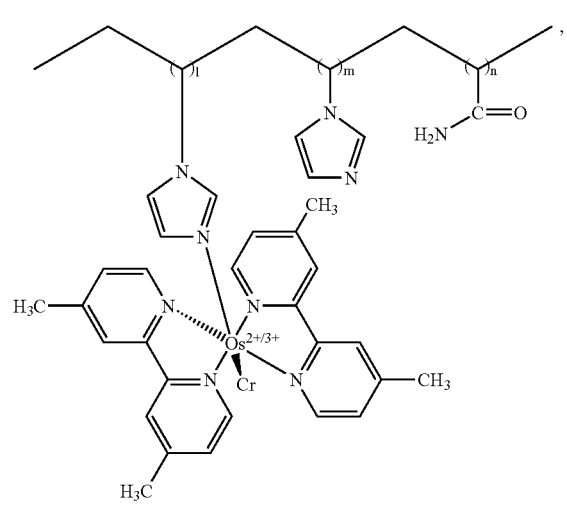

wherein each of l, m and n is independently a positive number;

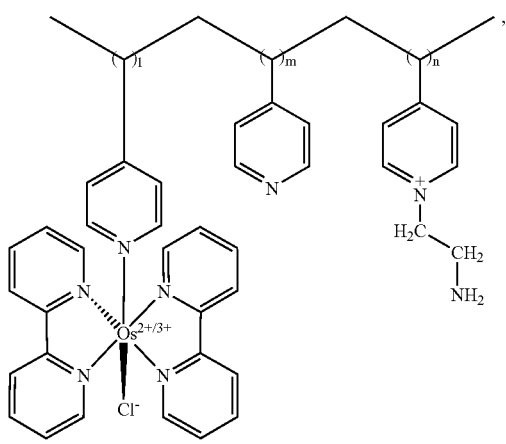

wherein each of l, m and n is independently a positive number;

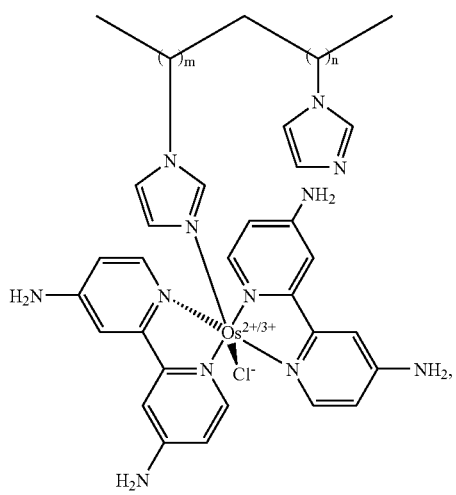

wherein each of m and n is independently a positive number; and

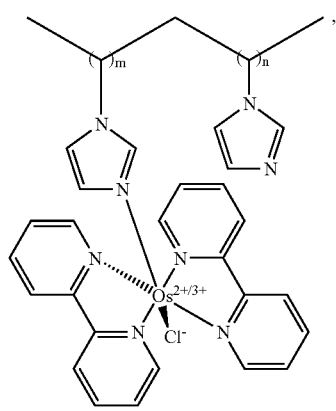

wherein each of m and n is independently a positive number.

22. The method of claim 1, wherein the redox polymers are selected from:
- poly(4-vinylimidazole-co-acrylamide) partially complexed with $[Os(2,2'\text{-bipyridine})_2Cl]^{+/2+}$;
- poly(1-vinylimidazole-co-acrylamide) partially complexed with $[Os(4,4'\text{-dimethyl-}2,2'\text{-bipyridine})_2Cl]^{+/2+}$;
- poly(4-vinylpyridine-co-acrylamide) partially complexed with $[Os(2,2'\text{-bipyridine})_2Cl]^{+/2+}$;
- poly(4-vinylpyridine) partially complexed with $[Os(2,2'\text{-bipyridine})_2Cl]^{+/2+}$ and partially quaternized with 2-bromoethylamine;
- poly(N-vinylimidazole) partially complexed with $[Os(4,4'\text{-diamino-}2,2'\text{-bipyridine})_2Cl]^{+/2+}$; and
- poly(N-vinylimidazole) partially complexed with $[Os(2,2'\text{-bipyridine})_2Cl]^{+/2+}$.

23. The method of claim 1, wherein the transition metal is selected from osmium and ruthenium.

24. The method of claim 1, wherein the first ligand is selected from a halide, a pseudohalide, and a perchlorate.

25. The method of claim 1, wherein the first ligand comprises chloride.

26. The method of claim 1, wherein the first ligand is labile.

27. The method of claim 1, wherein the first ligand is weakly coordinating.

28. The method of claim 1, wherein the first ligand is anionic.

29. The method of claim 1, wherein the second ligand is selected from an amine, a pyridine, an imidazole, and any derivative thereof.

30. The method of claim 1, wherein the second ligand is strongly coordinating.

31. The method of claim 1, wherein electrodepositing the redox polymers comprises electroreduction of the transition metal.

32. The method of claim 1, wherein the potential is from about −0.8 V to about −1.6 V.

33. The method of claim 1, wherein the cycle of varied potential comprises a negative potential and a positive potential relative to a redox potential of the redox polymers.

34. The method of claim 33, wherein the cycle of varied potential comprises a cycle of square-wave potentials.

35. The method of claim 33, wherein the at least one cycle comprises about 10 to about 200 cycles.

36. The method of claim 33, wherein the at least one cycle comprises about 50 to about 60 cycles.

37. The method of claim 33, wherein at least one of the negative potential and the positive potential is applied for from about 0.5 second to about 4 seconds.

38. The method of claim 33, wherein at least one of the negative potential and the positive potential is applied for about 2 seconds.

39. The method of claim 33, wherein the negative potential is in a range of up to about −150 mV relative to the redox potential of the redox polymers.

40. The method of claim 33, wherein the positive potential is in a range of up to about +150 mV relative to the redox potential of the redox polymers.

41. The method of claim 33, wherein prior to the application of the at least one cycle of varied potential, the electrode surface is oxidized via a plasma.

42. The method of claim 33, wherein prior to the application of the at least one cycle of varied potential, the electrode surface is electrooxidized and a potential of greater than about +0.5 V relative to a standard calomel electrode is applied to the electrode surface.

43. The method of claim 1, wherein electrodeposition of the redox polymers is irreversible.

44. The method of claim 1, wherein the redox polymer film has a redox potential above a redox potential of the redox polymers.

45. The method of claim 1, wherein the redox polymer film is electron- or hole-conducting.

46. The method of claim 1, wherein electrodepositing the redox polymers further comprises electrodepositing a redox enzyme on at least the portion of the electrode surface.

47. The method of claim 46, wherein the redox enzyme comprises a function selected from transition metal-coordinating lysine, histidine and/or arginine.

48. The method of claim 46, wherein the redox enzyme is selected from an oxidase, a peroxidase, and a copper-containing enzyme.

49. The method of claim 46, wherein the redox enzyme is selected from glucose oxidase, horseradish peroxidase, soybean peroxidase, a laccase, and a bilirubin oxidase.

50. The method of claim 46, further comprising, after electrodepositing the redox polymers, electrocatalytically oxidizing or reducing a substrate of the redox enzyme on at least the portion of the electrode surface.

51. The method of claim 50, wherein the substrate is selected from glucose, hydrogen peroxide, and oxygen.

52. The method of claim 1, wherein electrodepositing the redox polymers further comprises incorporating at least one oligonucleotide having a terminal amine into the redox polymer film.

53. The method of claim 1, further comprising:
providing at least one oligonucleotide at the electrode surface; and
incorporating the oligonucleotide into the redox polymer film.

54. The method of claim 53, wherein incorporating the oligonucleotide comprises forming a coordinative bond between the oligonucleotide and a transition metal complex of the redox polymer film.

55. The method of claim 53, wherein the oligonucleotide has a terminal amine and incorporating the oligonucleotide comprises forming a coordinative bond between the terminal amine of the oligonucleotide and a transition metal complex of the redox polymer film.

56. The method of claim 53, wherein the incorporating is irreversible.

57. The method of claim 53, further comprising, after the incorporating, electrodepositing redox polymers to form another redox polymer film.

58. The method of any one of claims 53 and 57, further comprising hybridizing the oligonucleotide of the oligonucleotide-incorporated film with a target oligonucleotide.

59. The method of claim 58, further comprising hybridizing the target oligonucleotide with an enzyme-labeled oligonucleotide.

60. The method of claim 59, wherein the enzyme-labeled oligonucleotide and the redox polymer film are in electrical communication.

61. The method of claim 59, further comprising, after hybridizing the target oligonucleotide with the enzyme-labeled oligonucleotide, electrocatalytically oxidizing or reducing a substrate of the enzyme on at least the portion of the electrode surface.

62. The method of claim 61, wherein the substrate is selected from glucose, hydrogen peroxide, and oxygen.

63. The method of any one of claims 50 and 61, further comprising measuring a current associated with electrocatalytic oxidation or reduction of the substrate of the enzyme.

64. Method of modifying an electrode surface, comprising:
providing an electrode surface;
providing redox polymers at the electrode surface, each redox polymer comprising a first anionic ligand and a second ligand; and
electrodepositing the redox polymers to form a redox polymer film on at least a portion of the electrode surface via application of a potential or at least one cycle of varied potential, the electrodepositing comprising coordinative crosslinking of the first ligand of a first redox polymer with the second ligand of the first redox polymer or the second ligand of a second redox polymer.

65. Method of modifying an electrode surface, comprising:
providing an electrode surface;
providing redox polymers at the electrode surface, each redox polymer comprising a first ligand and a second ligand; and
electrodepositing the redox polymers to form a redox polymer film on at least a portion of the electrode surface via application of a potential or at least one cycle of varied potential, the electrodepositing comprising coordinative crosslinking of the first ligand of a first redox polymer with the second ligand of the first redox polymer or the second ligand of a second redox polymer.

66. Method of modifying an electrode surface, comprising:
providing an electrode surface;
providing redox polymers at the electrode surface, each redox polymer comprising a complex of a transition metal, a first ligand, and a second ligand; and
electrodepositing the redox polymers to form a redox polymer film on at least a portion of the electrode surface via application of a potential or at least one cycle of varied potential, the electrodepositing comprising coordinative crosslinking of the first ligand of a first redox polymer with the second ligand of the first redox polymer or the second ligand of a second redox polymer.

* * * * *